(12) United States Patent
Cho et al.

(10) Patent No.: US 8,467,870 B2
(45) Date of Patent: Jun. 18, 2013

(54) TECHNIQUES FOR MODIFYING BREATHING RATE USING CARDIAC PACING

(75) Inventors: Yong Kyun Cho, Maple Grove, MN (US); Mark K. Erickson, Brooklyn Park, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/103,839

(22) Filed: May 9, 2011

(65) Prior Publication Data

US 2012/0290032 A1  Nov. 15, 2012

(51) Int. Cl.
*A61N 1/00* (2006.01)
(52) U.S. Cl.
USPC .......................................................... 607/20
(58) Field of Classification Search
USPC ..................................... 607/20, 42
See application file for complete search history.

(56) References Cited

U.S. PATENT DOCUMENTS

| | | | |
|---|---|---|---|
| 4,567,892 A | 2/1986 | Plicchi et al. | |
| 5,058,583 A | 10/1991 | Geddes et al. | |
| 5,562,712 A | 10/1996 | Steinhaus et al. | |
| 5,792,196 A | 8/1998 | Cooper et al. | |
| 5,964,788 A | 10/1999 | Greenhut | |
| 6,126,611 A | 10/2000 | Bourgeois et al. | |
| 6,141,590 A * | 10/2000 | Renirie et al. | 607/20 |
| 6,161,042 A | 12/2000 | Hartley et al. | |
| 6,305,943 B1 | 10/2001 | Pougatchev et al. | |
| 6,941,170 B1 | 9/2005 | Lu | |
| 7,171,270 B1 | 1/2007 | Park et al. | |
| 7,343,199 B2 | 3/2008 | Hatlestad et al. | |
| 7,539,539 B1 | 5/2009 | Bharmi | |
| 2003/0153955 A1 | 8/2003 | Park et al. | |
| 2005/0109338 A1 | 5/2005 | Stahmann et al. | |
| 2007/0179542 A1 | 8/2007 | Prakash et al. | |
| 2007/0250127 A1 | 10/2007 | Stylos et al. | |
| 2008/0071317 A1 | 3/2008 | Stahmann et al. | |
| 2010/0305647 A1 | 12/2010 | Mccabe et al. | |

FOREIGN PATENT DOCUMENTS

WO  2007122406 A1  11/2007

OTHER PUBLICATIONS

U.S. Appl. No. 131/103,861, by Yong Kyun Cho, filed May 9, 2011.
Hayano et al., "Respiratory Sinus Arrhythmia," Circulation 1996;94:842-847.
Hayano et al., "Effects of respiratory interval on vagal modulation of heart rate," Am. J. Physiol. 267 (Heart Circ. Physiol. 36): H33-H40, 1994.

(Continued)

*Primary Examiner* — Christopher D Koharski
*Assistant Examiner* — Philip Edwards
(74) *Attorney, Agent, or Firm* — Reed A. Duthler; Stephen W. Bauer

(57) ABSTRACT

A method includes controlling a cardiac pacing rate of an implantable medical device (IMD) to control a heart rate of a patient and determining that the patient is in a resting state. The method further includes modifying the pacing rate of the IMD for N cardiac cycles in response to determining that the patient is in the resting state. N is an integer greater than 1. Modifying the pacing rate includes incrementally increasing the pacing rate for a first portion of the N cardiac cycles, and incrementally decreasing the pacing rate for a second portion of the N cardiac cycles.

22 Claims, 10 Drawing Sheets

OTHER PUBLICATIONS

Hayano et al., "Hypothesis: respiratory sinus arrhythmia is an intrinsic resting function of cardiopulmonary system," Cardiovascular Research 58 (2003): 1-9.

Hayano et al., "Assessment of frequency shifts in R-R interval variability and respiration with complex demodulation," J. Appl. Physiol. 77(6):2879-2988, 1994.

Eckberg et al.,"The human respiratory gate," J. Physiol (2003) 548.2, pp. 339-352.

Office Action from U.S. Appl. No. 13/103,861 dated May 29, 2012.

Response to Office Action dated May 29, 2012 from U.S. Appl. No. 13/103,861 filed on Jul. 13, 2012.

P0034195.00 (PCT/US2012/036927) PCT Notification of Transmittal of the International Search Report and the Written Opinion of the International Searching Authority.

Office Action from U.S. Appl. No. 13/103,861 dated Nov. 6, 2012.

Amendment from related U.S. Appl. No. 13/103,861 filed on Dec. 12, 2012.

Advisory Action from related U.S. Appl. No. 13/103,861 dated Dec. 31, 2012.

Pre-Appeal Brief Request for Review from related U.S. Appl. No. 13/103,861 filed on Jan. 22, 2013.

Notice of Appeal from related U.S. Appl. No. 13/103,861 filed on Jan. 22, 2013.

\* cited by examiner

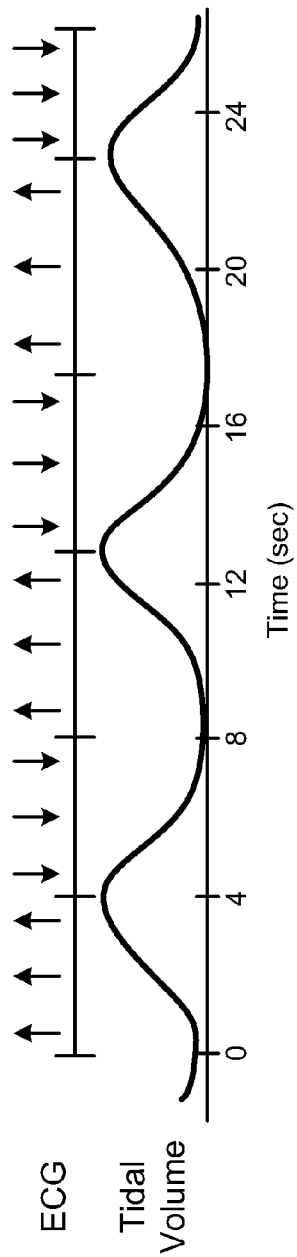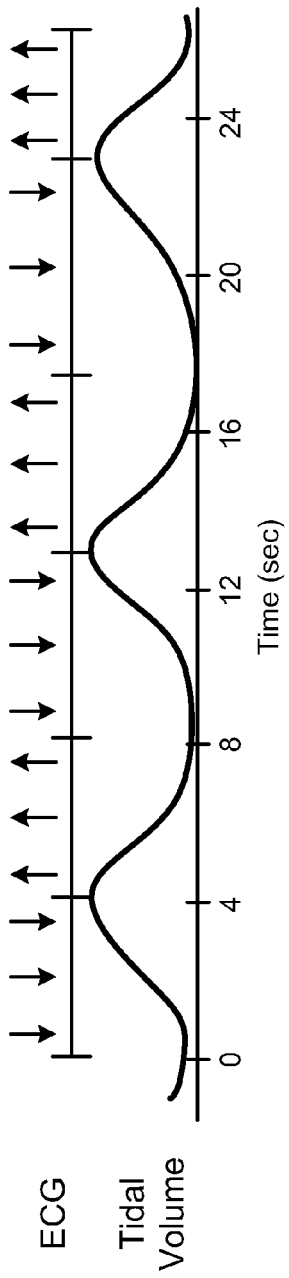

TECHNIQUES FOR MODIFYING BREATHING RATE USING CARDIAC PACING

TECHNICAL FIELD

The disclosure relates to techniques for modifying breathing of a patient, and more particularly, to modifying a breathing rate of the patient using cardiac pacing.

BACKGROUND

A phase relationship may exist between cardiac cycle frequency and breathing cycle frequency in a person, with the breathing cycle frequency being somewhat less than the cardiac cycle frequency. The chemical makeup of the blood, e.g., the oxygen and carbon dioxide concentrations within the blood, may also have some phase relationship with respect to blood flow and the phase of the breathing cycle. Respiratory sinus arrhythmia (RSA) is a phenomenon that reflects such a phase relationship between the breathing cycle and the cardiac cycle. RSA describes a variation in heart rate that occurs during a breathing cycle. During RSA, a person's heart rate may accelerate during inhalation and decelerate during exhalation. RSA may improve pulmonary gas exchange, and may be more efficient in cardiopulmonary energy consumption compared to a constant heart rate. In some examples, RSA may be more prevalent in a younger person, and may be lost as the person ages, or lost due to other pathology.

SUMMARY

An IMD, or other device, of the present disclosure may generate a cardiac pacing pattern according to a set of modified pacing parameters in order to control a breathing rate of a patient. The IMD may modulate cardiac pacing when one or more initial conditions are satisfied. In some examples, the initial conditions may indicate that the patient is in a resting state (e.g., at rest and/or inactive). The one or more initial conditions may include, but are not limited to, at least one of the heart rate of the patient, the activity level of the patient, and the posture of the patient. Implementation of the modified pacing parameters over a period of time while the initial conditions are satisfied (e.g., while the patient is at rest and/or inactive) may cause the patient's breathing pattern to align with the cardiac pacing pattern.

In some examples, the IMD may produce a pacing pattern that is similar to that observed during respiratory sinus arrhythmia (RSA). Over a period of time, the breathing pattern of the patient may tend to align with this pacing pattern such that the relative timing of the breathing pattern and the pacing pattern may imitate RSA. The delivery of this pacing pattern may benefit the patient by establishing a phase relationship between the cardiac cycle and the breathing cycle of the patient that is more optimal to the patient. These pacing patterns implemented by the IMD may enhance cardiopulmonary vagal activity and improve pulmonary gas exchange, and in turn, lower the blood pressure of the patient.

In some examples, the IMD may provide a pacing pattern that is inverse to the RSA pacing pattern. For example, the IMD may incrementally decrease the pacing rate of the device upon detection of inhalation, and may incrementally increase the pacing rate upon the detection of exhalation. Inverse RSA may cause pulmonary gas exchange to be impeded. For example, inverse RSA may cause an increase in carbon dioxide in the blood (e.g., an increased PaCO2). The increased level of carbon dioxide in the blood may in turn promote an increased breathing rate and/or tidal volume. The IMD of the present disclosure may implement inverse RSA pacing to control respiration in those patients with inadequate breathing patterns. For example, IRSA pacing may be implemented in those patients having sleep apnea (e.g., central sleep apnea) in order to increase the breathing rate of the patient.

In some examples according to the present disclosure, a method comprises controlling a cardiac pacing rate of an IMD to control a heart rate of a patient and determining that the patient is in a resting state. The method further comprises modifying the pacing rate of the IMD for N cardiac cycles in response to determining that the patient is in the resting state. N is an integer greater than 1. Modifying the pacing rate comprises incrementally increasing the pacing rate for a first portion of the N cardiac cycles, and incrementally decreasing the pacing rate for a second portion of the N cardiac cycles.

In other examples according to the present disclosure, a device comprises one or more electrodes configured for implantation in a patient, a stimulation module configured to generate stimulation for delivery to the one or more electrodes, and a processing module. The processing module controls a cardiac pacing rate of the stimulation delivered to the one or more electrodes to control a heart rate of the patient, determines that the patient is in a resting state, and modifies the pacing rate for N cardiac cycles in response to determining that the patient is in the resting state. N is an integer greater than 1. Modifying the pacing rate comprises incrementally increasing the pacing rate for a first portion of the N cardiac cycles, and incrementally decreasing the pacing rate for a second portion of the N cardiac cycles.

In other examples according to the present disclosure, a system comprises means for controlling a cardiac pacing rate of an IMD to control a heart rate of a patient, means for determining that the patient is in a resting state, and means for modifying the pacing rate of the IMD for N cardiac cycles in response to determining that the patient is in the resting state. N is an integer greater than 1. Modifying the pacing rate comprises incrementally increasing the pacing rate for a first portion of the N cardiac cycles, and incrementally decreasing the pacing rate for a second portion of the N cardiac cycles.

In other examples according to the present disclosure, a computer-readable storage medium comprises instructions that cause a programmable processor to control a cardiac pacing rate of an IMD to control a heart rate of a patient, determine that the patient is in a resting state, and modify the pacing rate of the IMD for N cardiac cycles in response to determining that the patient is in the resting state. N is an integer greater than 1. Modifying the pacing rate comprises incrementally increasing the pacing rate for a first portion of the N cardiac cycles, and incrementally decreasing the pacing rate for a second portion of the N cardiac cycles.

In still other examples according to the present disclosure, a method comprises controlling a cardiac pacing rate of an IMD to control a heart rate of a patient, detecting inhalation and exhalation of the patient, and determining that the patient is in a resting state. The method further comprises, in response to determining that the patient is in the resting state, incrementally increasing the pacing rate while exhalation of the patient is detected, and incrementally decreasing the pacing rate while inhalation of the patient is detected.

In other examples according to the present disclosure, a device comprises one or more electrodes configured for implantation in a patient, a stimulation module configured to generate stimulation for delivery to the one or more electrodes, and a processing module. The processing module is configured to control a pacing rate delivered to the one or more electrodes to control a heart rate of the patient, detect inhalation and exhalation of the patient, and determine that the patient is in a resting state. In response to determining that the patient is in the resting state, the processing module incrementally increases the pacing rate while exhalation of the patient is detected, and incrementally decreases the pacing rate while inhalation of the patient is detected.

In other examples according to the present disclosure, a system comprises means for controlling a cardiac pacing rate of an IMD to control a heart rate of a patient, means for detecting inhalation and exhalation of the patient, and means for determining that the patient is in a resting state. The system further comprises, in response to determining that the patient is in the resting state, means for incrementally increasing the pacing rate while exhalation of the patient is detected, and means for incrementally decreasing the pacing rate while inhalation of the patient is detected.

In other examples, a computer-readable storage medium comprises instructions that cause a programmable processor to control a cardiac pacing rate of an IMD to control a heart rate of a patient, detect inhalation and exhalation of the patient, and determine that the patient is in a resting state. The computer-readable storage medium further comprises instructions that cause the programmable processor to, in response to determining that the patient is in the resting state, incrementally increase the pacing rate while exhalation of the patient is detected, and incrementally decrease the pacing rate while inhalation of the patient is detected.

The details of one or more examples are set forth in the accompanying drawings and the description below. Other features, objects, and advantages will be apparent from the description and drawings, and from the claims.

BRIEF DESCRIPTION OF THE DRAWINGS

FIG. 8A is a graph showing modulation of pacing parameters to imitate respiratory sinus arrhythmia (RSA) based on a detected phase of the breathing cycle.

FIG. 8B is a graph showing inverse RSA pacing based on a detected phase of the breathing cycle.

DETAILED DESCRIPTION

Figure 1:
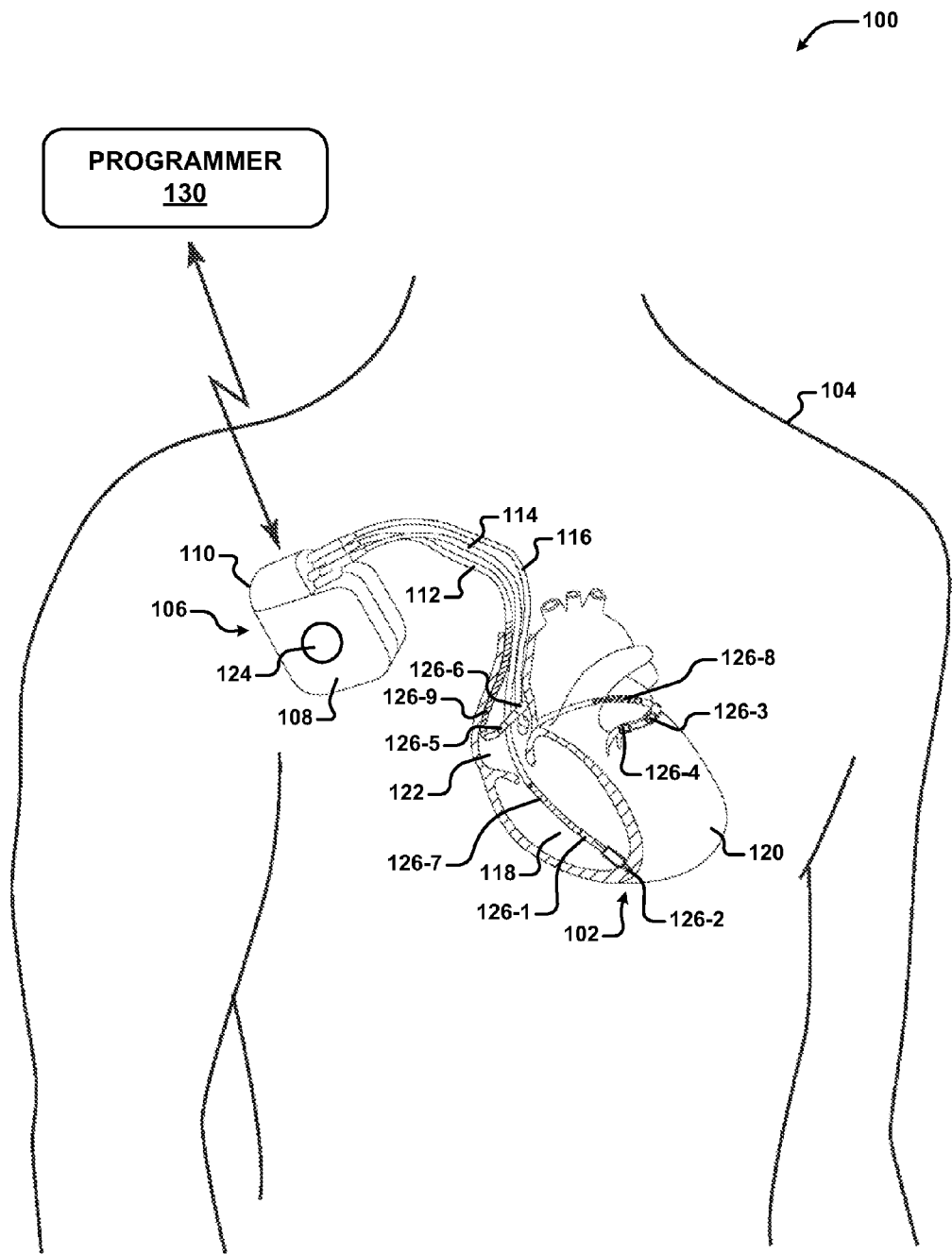
FIG. 1 is a conceptual diagram of an example system that may be used to monitor breathing parameters of a patient and provide therapy to a heart of the patient.

An IMD, e.g., a pacemaker and/or cardioverter-defibrillator, of the present disclosure may control a breathing rate of a patient by modulating a cardiac pacing rate. For example, the IMD may control the breathing rate of the patient by modulating the cardiac pacing rate according to a set of modified pacing parameters. The breathing rate of the patient may be a number of breathing cycles (i.e., breaths taken by the patient) per unit of time. Each breathing cycle may include a period of time during which the patient inhales (i.e., an inhalation phase) and a period of time during which the patient exhales (i.e., an exhalation phase). The modified pacing parameters may include, but are not limited to, modified pacing rates, a number of cardiac cycles for which the pacing rates will be modified over a period of time or over a specified number of cardiac cycles, and a number of breathing cycles for which pacing rates will be modified over a period of time or over a specified number of breathing cycles.

The IMD of the present disclosure may be configured to control the pacing rate of a patient's heart in order to cause the patient's breathing rate to reach a target breathing rate. The target breathing rate may be described as a breathing rate that the IMD is configured to achieve via modulation of the pacing rate. The target breathing rate may be a breathing rate that may be selectively chosen, e.g., by a clinician, such that the target breathing rate may provide a variety of benefits to the patient. In examples where the patient has high blood pressure (e.g., chronic high blood pressure), the target breathing rate may be selected to be a consistent and slow breathing rate relative to the typical breathing rate of the patient. This consistent and slow breathing rate may tend to improve pulmonary gas exchange, and in turn, lower the blood pressure of the patient. In other patients, the IMD may generate pacing in order to increase breathing rate, e.g., to provide benefits to patients having sleep apnea (e.g., central sleep apnea).

The target breathing rate may be described as a future desirable breathing rate which the pacemaker attempts to achieve via pacing rate modulation. In some scenarios, a current breathing rate of the patient may differ from the target breathing rate, e.g., the current breathing rate may be greater or less than the target breathing rate. In these scenarios, modulation of the pacing rate according to the modified pacing parameters may cause the breathing rate to align with the target breathing rate. In other words, in these scenarios, the IMD may be configured to modulate pacing rate in order to cause an increase or decrease in the patient's current breathing rate so that the patient's future breathing rate reaches the target breathing rate. In other scenarios, a current breathing rate of the patient may be approximately equal to the target breathing rate. In these scenarios, modulation of the pacing rate according to the modified pacing parameters may cause the breathing rate of the patient to be maintained at approximately the target breathing rate. In other words, in these scenarios, the IMD may be configured to modulate the pacing rate in order to maintain the patient's current breathing rate at, or around, the target breathing rate.

The IMD may modulate cardiac pacing according to the modified pacing parameters in order to control the breathing rate of the patient when the IMD determines that one or more initial conditions are satisfied. The one or more initial conditions, when satisfied, may indicate that the patient is in a resting state. While in the resting state, the patient may be at rest or may be relatively inactive. In some examples, the patient may be awake while in the resting state, but engaged in little to no activity. In other examples, the patient may be asleep while in the resting state. The patient may exit the resting state upon resuming activity, such as moderate exercise or other physical exertion. Implementation of the modified pacing parameters over a period of time while the one or more initial conditions are satisfied (i.e., while the patient is in the resting state) may cause the patient's breathing pattern to align with the cardiac pacing pattern. Upon detection of one or more of the initial conditions, the IMD may modulate cardiac pacing according to the modified pacing parameters. Otherwise, while the IMD does not detect one or more of the initial conditions, the IMD may pace the patient normally, e.g., according to typical patient parameters for that patient. In some examples, the IMD may pace in a DDDR mode, in which case the patient may typically be paced at a programmed lower rate when there is no sensor-based input to change the pacing rate. The lower rate may typically be set between approximately 40 and 80 beats per minute in most patients.

Detection of one or more of the initial conditions may reliably indicate that the patient is in the resting state (e.g., at rest and/or inactive), while absence of the initial conditions may indicate that patient is not likely at rest and/or active. The initial conditions may include, but are not limited to, a heart-rate initial condition, an activity-level initial condition, and a posture-based initial condition. The IMD may monitor at least one of the heart rate of the patient, the activity level of the patient, and the posture of the patient to determine whether any of the initial conditions are satisfied, e.g., to determine whether the patient is in the resting state (e.g., resting and/or inactive). In general, the heart-rate initial condition may be satisfied when the heart rate is less than a threshold heart rate for a predetermined period of time. The activity-level initial condition may be satisfied when the activity level of the patient is less than a threshold amount of activity, e.g., as determined based on measurements of patient activity from an accelerometer. The posture-based initial condition may be satisfied when the posture of the patient indicates that the patient may be inactive and/or in a resting posture (e.g., lying down).

Although the IMD may determine whether initial conditions are satisfied based on at least one of the heart rate of the patient, the activity level of the patient, and the posture of the patient, in other examples, the IMD may determine that the initial conditions are satisfied based on other measured parameters, e.g., based on respiration parameters measured by a respiration (impedance) sensor, based on pressure parameters measured by least one of an intracardiac pressure sensor or intravascular pressure sensor, based on heart sound parameters measured by a heart sound sensor, and based on optical (oxygenation) parameters measured by an optical sensor.

In some examples, the IMD may modulate cardiac pacing in order to control the patient's breathing rate without measuring breathing parameters of the patient. Breathing parameters may include any parameters that may be measured by the IMD that indicate a breathing phase or breathing rate of the patient. In some examples, the IMD may measure breathing parameters of the patient by measuring a thoracic impedance of the patient. In examples where the IMD does not measure breathing parameters, and therefore does not use breathing parameters of the patient as feedback to control cardiac pacing, the IMD may be referred to as operating in an "open-loop mode." Operation of the IMD in the open-loop mode is described with respect to FIGS. 4 and 5.

The IMD may modify the pacing rate in open-loop mode according to the modified pacing parameters when one or more of the initial conditions are satisfied. The modified pacing parameters may include, but are not limited to, a total number of cardiac cycles for which the pacing will be modified over a period of time, a total number of breathing cycles for which pacing will be modified over a period of time, a pacing rate increment value, and a pacing rate decrement value. Generally, the IMD may implement the modified pacing parameters in the open-loop mode in order to maintain the patients breathing rate at a more consistent rate and/or in order to slow the patient's breathing rate.

The modified pacing parameters implemented by the IMD may be selected such that a patient's target breathing rate is reached when the IMD modulates pacing according to the modified pacing parameters. The modified pacing parameters may be patient-specific pacing parameters. Such patient specific parameters may be determined by a clinician based, for example, on diagnostic tests performed on the patient. Such diagnostic tests may include, for example, determination of the resting heart rate of the patient, determination of the resting breathing rate of the patient, determination of a heart rate at which the breathing control of the present disclosure should be initiated (e.g., a threshold heart rate), and determination of a breathing rate (at rest) for which the breathing control of the present disclosure could be initiated.

The IMD may implement the modified pacing parameters in open-loop mode to produce a pattern of pacing that is similar to that observed during respiratory sinus arrhythmia (RSA). During RSA, a patient's heart rate may accelerate during inhalation and decelerate during exhalation. Accordingly, while operating in the open-loop mode according to the modified pacing parameters, the IMD may incrementally increase (i.e., accelerate) the pacing rate for a number of cardiac cycles, then incrementally decrease (i.e., decelerate) the pacing rate for a number of cardiac cycles, and then repeat this pattern over a plurality of breathing cycles. For example, while operating in the open-loop mode according to the modified pacing parameters, the IMD may increase the pacing rate a plurality of times during successive cardiac cycles, then decrease the pacing rate a plurality of times during successive cardiac cycles.

The breathing pattern of the patient treated by the IMD in the open-loop mode may tend to align with the pacing pattern over time such that the relative timing of the breathing pattern and the pacing pattern may imitate RSA. In other words, after a period of time during which the IMD operates in the open-loop mode, the breathing pattern of the patient (e.g., the breathing rate and phase) may tend to align with the pacing pattern delivered according to the modified pacing parameters such that RSA is imitated. Note that such a correlation between the pacing pattern and the breathing pattern that may be present while the IMD is operating in the open-loop mode may be caused by pacing, and not initiated by breathing of the patient, as may be the case with typically observed RSA.

The modified pacing parameters programmed into a patient's IMD for operation in the open-loop mode may be set based on the patient's typical breathing rate and resting heart rate. In these examples, a pacing pattern similar to RSA may be generated based on, for example, a target breathing rate that may be approximately equal to the patient's typical breathing rate. In general, the modified pacing parameters may be set so that pacing causes the patient's breathing rate to reach a target breathing rate that is similar to, or lower than, the patients typical breathing rate.

Figure 6:
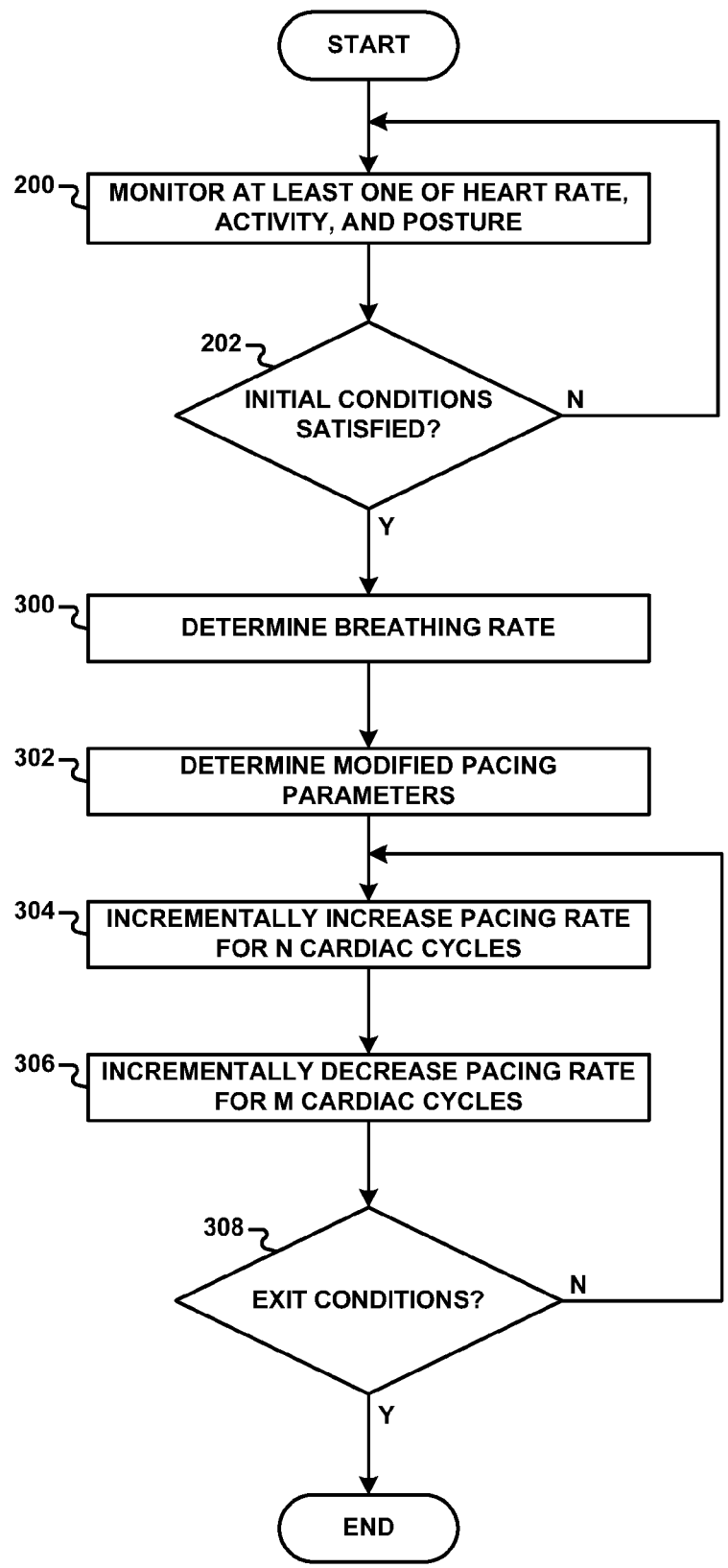
FIGS. 6 and 7 are flow diagrams showing a method for controlling a breathing rate of the patient via cardiac pacing modulation based on a sensed breathing rate.
Figure 7:
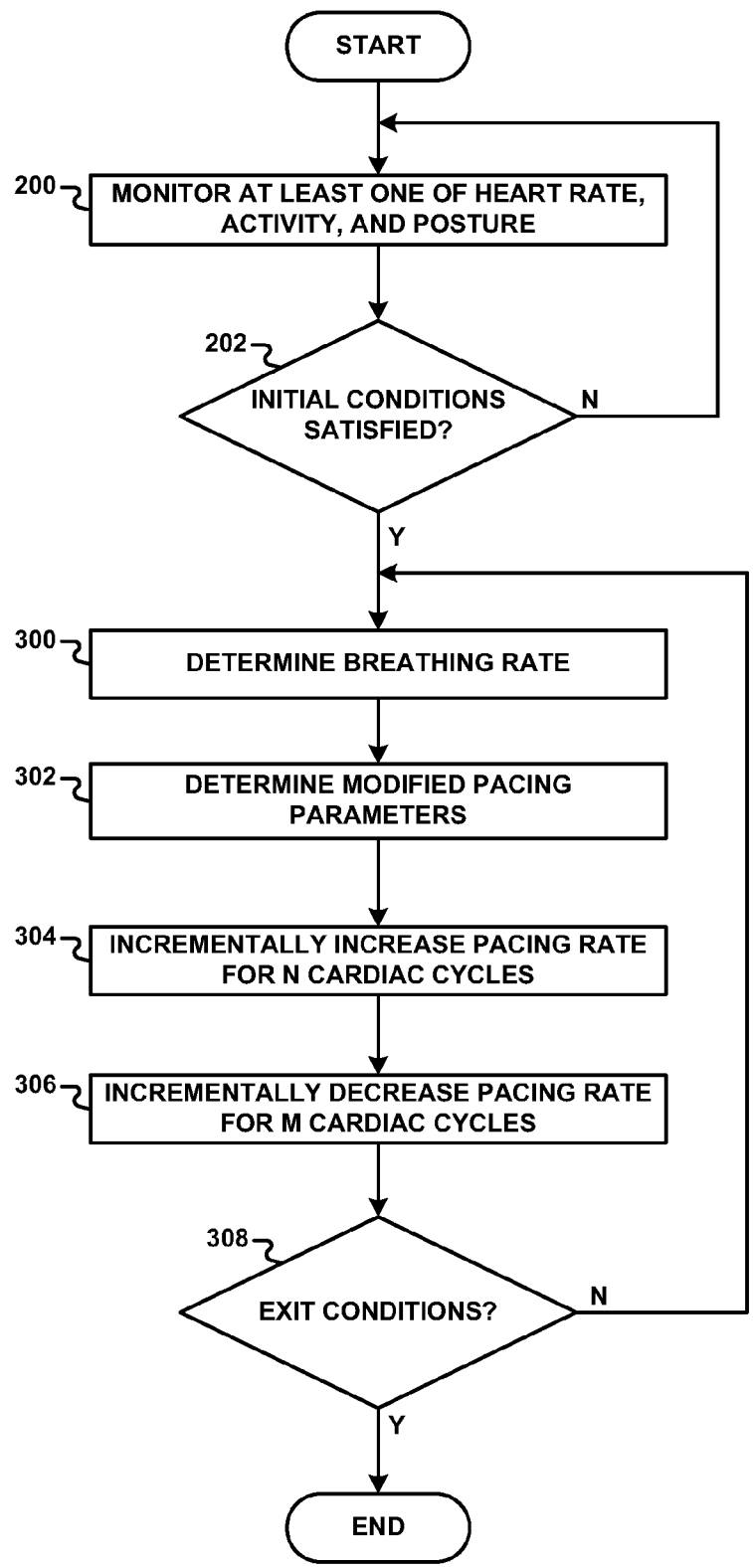

In other examples, with respect to FIGS. 6 and 7, the IMD may modulate cardiac pacing in order to control the breathing rate of the patient based on one or more breathing parameters measured by the IMD. In some examples, with respect to FIG. 6, the IMD may determine a current breathing rate of the patient when one or more of the initial conditions are satisfied (e.g., while the patient is resting and/or inactive), then subsequently modulate cardiac pacing in a pattern similar to RSA in order to control the breathing rate without further measurements of breathing parameters. In these examples, the IMD may measure a breathing rate (e.g., a resting breathing rate), determine modified pacing parameters based on the measured breathing rate, and then control cardiac pacing based on the modified pacing parameters for a predetermined period of time without measuring breathing parameters of the patient.

In still other examples, with respect to FIG. 7, the IMD may modulate cardiac pacing in order to control the breathing rate of the patient based on more frequent measurements of breathing parameters. In these examples, the IMD may determine the breathing rate of the patient after pacing for a predetermined number of breathing cycles, e.g., 1 or more breathing cycles. In other examples, the IMD may determine the breathing rate of the patient after pacing for a predetermined amount of time, e.g., on the order of minutes (i.e., tens of breathing cycles).

Although the techniques of FIGS. 4-7 may be directed to cardiac pacing that is aimed at causing a more consistent and/or slow breathing rate in the patient, in other examples, the IMD of the present disclosure may be directed to increasing the breathing rate of the patient. As described herein with respect to FIGS. 8-9, the IMD may provide cardiac pacing, based on measured breathing parameters, that may increase the breathing rate of the patient to reach the target breathing rate. In these examples, the IMD may provide cardiac pacing based on the phase of respiration (e.g., inhalation or exhalation) as detected by the IMD.

For example, the IMD may incrementally decrease (i.e., decelerate) the pacing rate upon detection of inhalation, and may incrementally increase (i.e., accelerate) the pacing rate upon the detection of exhalation. In other words, the IMD may increase the pacing rate a plurality of times during successive cardiac cycles upon detection of exhalation, then decrease the pacing rate a plurality of times during successive cardiac cycles upon the detection of inhalation. Pacing in this manner may be referred to as "inverse RSA (iRSA) pacing," since this pattern of pacing may be inverse to RSA as described above in which heart rate accelerates upon inhalation and decelerates upon exhalation. Such iRSA pacing may cause an increase in carbon dioxide in the blood, e.g., an increased partial pressure of carbon dioxide ($PaCO_2$). The increased level of carbon dioxide in the blood may in turn promote an increased breathing rate and/or tidal volume.

In summary, the IMD of the present disclosure may implement various pacing techniques on a patient (e.g., a resting and/or inactive patient) to control the patient's breathing rate in order to reach a desired target breathing rate. In some examples, the IMD may provide open-loop pacing, e.g., without measurement of breathing parameters, to maintain or slow a patient's breathing rate, as described with respect to FIGS. 4-5. In other examples, the IMD may maintain or slow the patient's breathing rate based on measured breathing parameters, as described with respect to FIGS. 6-7. In still other examples, the IMD may provide inverse RSA pacing based on measurement of breathing parameters (e.g., breathing phase and rate) in order to increase the breathing rate of the patient, as described with respect to FIGS. 8B-9. In some examples, the IMD may selectively choose between the above techniques for decreasing, maintaining, and increasing the patient's breathing rate to reach a target breathing rate, as described with respect to FIG. 10. An example IMD that may implement the various pacing techniques described above in order to decrease, maintain, or increase a resting patient's breathing rate is now described in detail.

FIG. 1 shows an example system 100 that may be used to diagnose conditions of and provide therapy to a heart 102 of a patient 104. System 100 includes an IMD 106. For example, IMD 106 may be an implantable pacemaker, cardioverter, and/or defibrillator that monitors electrical activity of heart 102, monitors breathing parameters of patient 104, and provides electrical stimulation to heart 102.

IMD 106 includes a housing 108 and a connector block 110. Housing 108 and connector block 110 may form a hermetic seal that protects components of IMD 106. IMD 106 is coupled to leads 112, 114, and 116 via connector block 110. Leads 112, 114, 116 extend into heart 102. Right ventricular lead 114 extends into right ventricle 118. Left ventricular coronary sinus lead 116 extends into the coronary sinus to a region adjacent to the free wall of left ventricle 120. Right atrial lead 112 extends into right atrium 122.

Housing 108 may enclose an electrical sensing module that monitors electrical activity of heart 102, and may also enclose a signal generator module that generates therapeutic stimulation, such as cardiac pacing pulses, anti-tachycardia pacing (ATP), cardioversion therapy, and/or defibrillation therapy. Leads 112, 114, 116 are coupled to the signal generator module and the electrical sensing module of IMD 106 via connector block 110.

Figure 2:
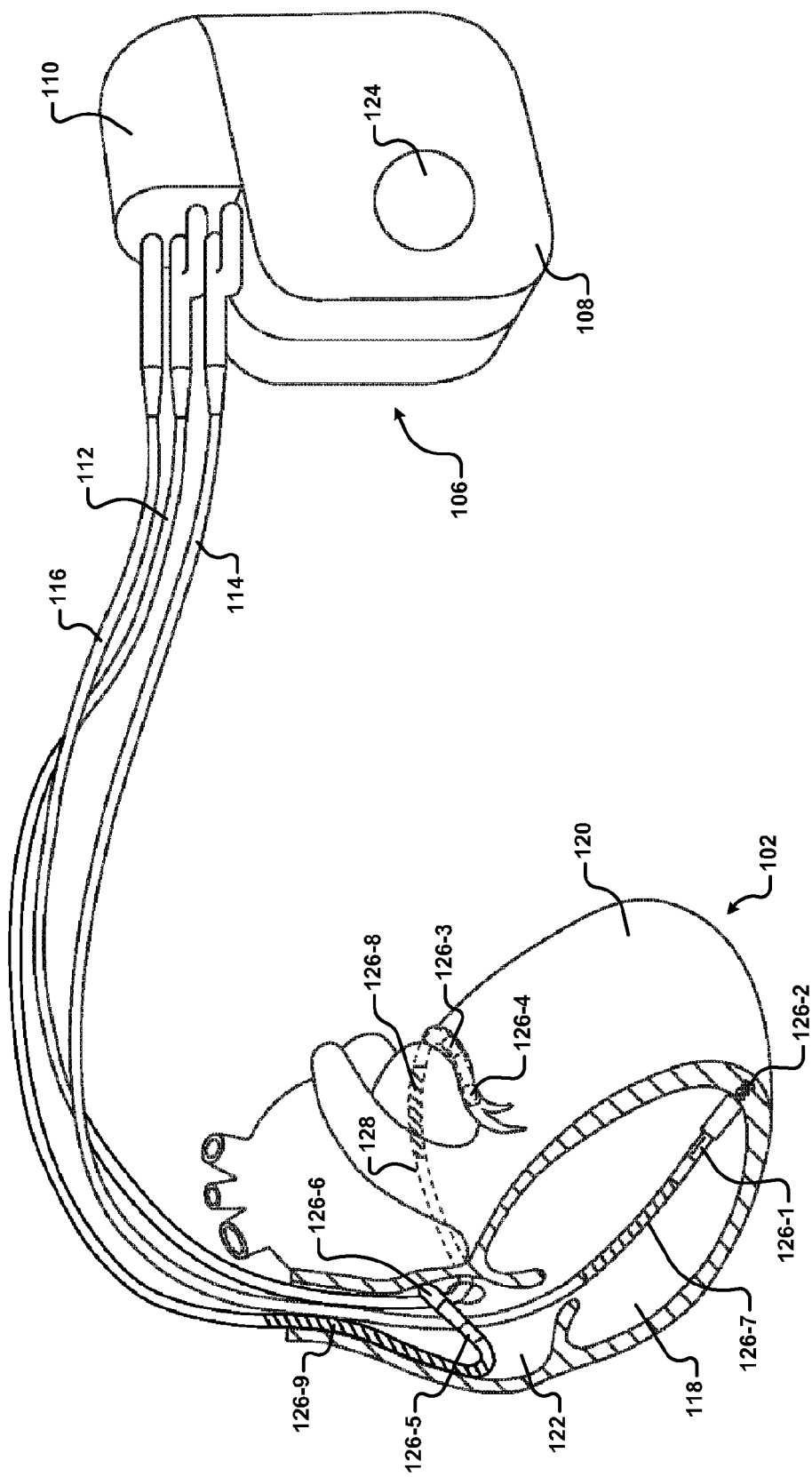
FIG. 2 is a conceptual diagram showing a more detailed view of an implantable medical device (IMD) of FIG. 1.

FIG. 2 shows a more detailed view of IMD 106 and leads 112, 114, 116. IMD 106 includes a housing electrode 124, which may be formed integrally with an outer surface of housing 108 of IMD 106 or otherwise coupled to housing 108. Although a single housing electrode 124 is illustrated in FIGS. 1-2, IMD 106 may include more or less than a single housing electrode 124.

Leads 112, 114, 116 include electrodes 126-1-126-9 (collectively "electrodes 126"). Lead 114 includes bipolar electrodes 126-1, 126-2 which are located in right ventricle 118. Lead 116 includes bipolar electrodes 126-3, 126-4 which are located in coronary sinus 128. Lead 112 includes bipolar electrodes 126-5, 126-6 which are located in right atrium 122. Electrodes 126-1, 126-3, 126-5 may take the form of ring electrodes. Electrodes 126-2, 126-4, 126-6 may take the form of, for example, helix tip electrodes or small circular electrodes at the tip of a tined lead or other fixation element. Leads 112, 114, 116 also include elongated electrodes 126-7, 126-8, 126-9, respectively, which may take the form of a coil. Although three leads 112, 114, 116, each including three electrodes, are illustrated, other configurations of leads and electrodes are contemplated.

IMD 106 may sense electrical activity of heart 102 and/or deliver electrical stimulation to heart 102 via electrodes 124, 126. IMD 106 may sense electrical activity using any combination of electrodes 124, 126. For example, IMD 106 may sense electrical activity via any bipolar combination of electrodes 126. Furthermore, any of electrodes 126 may be used for unipolar sensing in combination with housing electrode 124. IMD 106 may deliver pacing pulses via electrodes 124, 126 using a unipolar or bipolar combination of electrodes 124, 126. IMD 106 may deliver cardioversion pulses and/or defibrillation pulses to heart 102 via any combination of elongated electrodes 126-7, 126-8, 126-9, and housing electrode 124.

Using the signal generator module and the electrical sensing module, IMD 106 may provide pacing pulses to heart 102 based on the electrical signals sensed within heart 102. IMD 106 may also provide ATP therapy, cardioversion, and/or defibrillation therapy to heart 102 based on the electrical signals sensed within heart 102. For example, IMD 106 may detect an arrhythmia of heart 102, such as VT or VF, and deliver ATP therapy, cardioversion, or defibrillation therapy to heart 102 in response to the detection of VT/VF.

In some examples, IMD 106 may monitor breathing parameters of patient 104 via electrodes 124, 126. For example, IMD 106 may measure impedance (e.g., thoracic impedance) between any of electrodes 124, 126 and determine a variety of breathing parameters based on the measured impedance. IMD 106 may determine the breathing rate of patient 104 based on the measured impedance over a period of breathing cycles. Additionally, in some examples, IMD 106 may detect the breathing phase of patient 104, e.g., whether patient 104 is inhaling or exhaling. In some examples, IMD 106 may modulate the cardiac pacing rate based on at least one of the detected breathing rate of patient 104 and the breathing phase of patient 104.

Referring back to FIG. 1, system 100 may include a programmer 130. Programmer 130 may be a handheld computing device, desktop computing device, a networked computing device, etc. Programmer 130 may include a computer-readable storage medium having instructions that cause a processor of programmer 130 to provide the functions attributed to programmer 130 in the present disclosure.

Programmer 130 may include a telemetry head (not shown). IMD 106 and programmer 130 may wirelessly communicate with one another, e.g., transfer data between one another, via the telemetry head. For example, IMD 106 may send data to programmer 130, and programmer 130 may retrieve data stored in IMD 106 and/or program IMD 106.

Data retrieved from IMD 106 using programmer 130 may include cardiac EGMs and marker channel data stored by IMD 106 that indicate electrical activity of heart 102. Data transferred to IMD 106 using programmer 130 may include, for example, values for operational parameters, electrode selections used to deliver therapy, and/or modified pacing parameters, such as the amounts by which pacing rates may be incrementally increased or decreased, a number of cardiac cycles for which the pacing rates will be modified, and a number of breathing cycles for which pacing rates will be modified.

Figure 3:
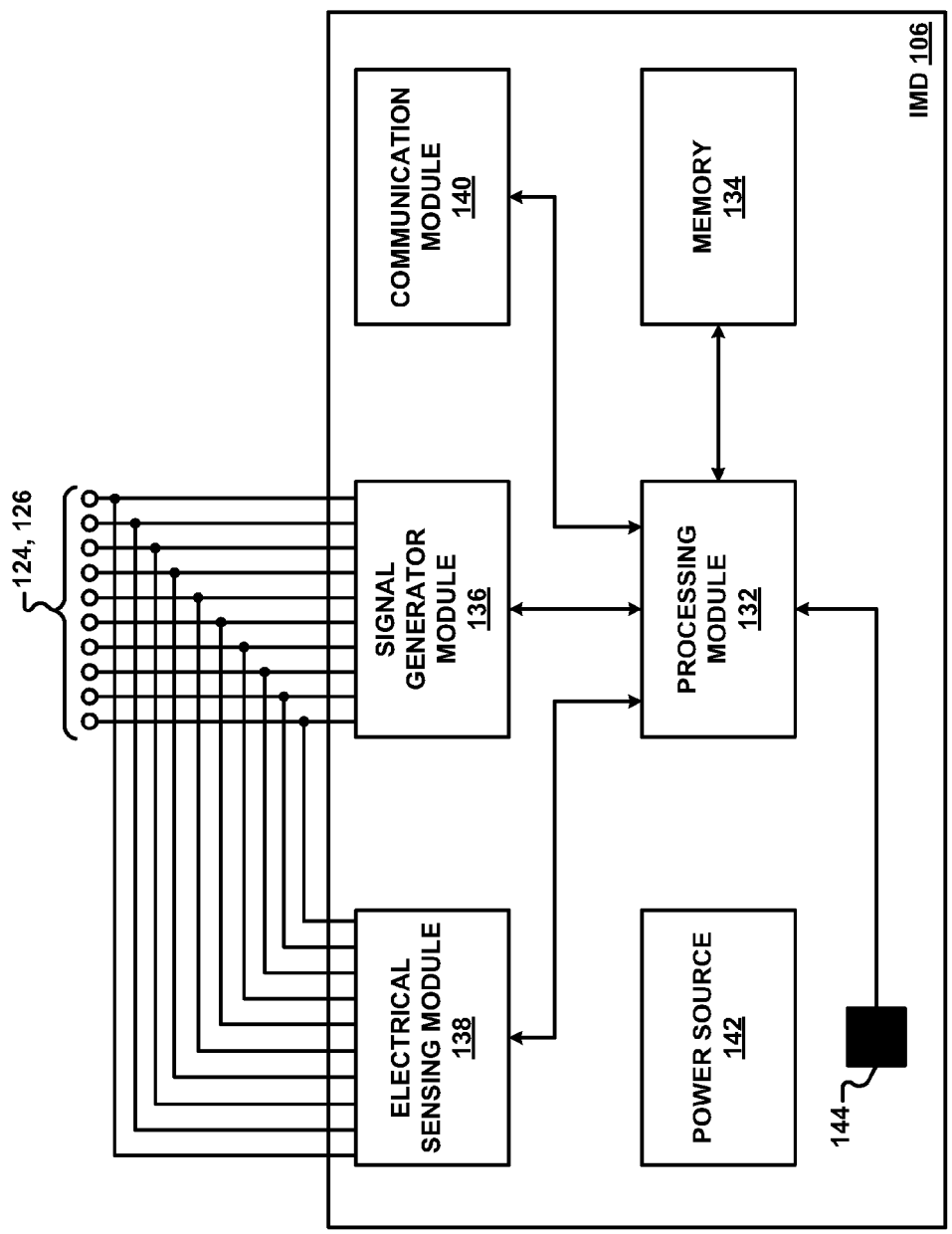
FIG. 3 is a functional block diagram showing the IMD of FIG. 1.

FIG. 3 shows a functional block diagram of an example IMD 106. IMD 106 includes a processing module 132, memory 134, a signal generator module 136, an electrical sensing module 138, a communication module 140, and a power source 142, such as a battery, e.g., a rechargeable or non-rechargeable battery. In some examples, IMD 106 may include one or more sensors (e.g., sensor 144) with which processing module 132 may communicate. For example, sensor 144 may comprise at least one of a motion sensor (e.g., an accelerometer and/or gyroscopic sensor), a heart sound sensor, or a pressure sensor (e.g., a capacitive sensor) that senses intracardiac or other cardiovascular pressure. Processing module 132 may determine, for example, an activity level of patient 104, a heart rate of patient 104, and intracardiac or other cardiovascular pressure based on data measured by one or more sensors 144.

In some examples, sensor 144, or another sensor in addition to sensor 144, may be located external to IMD 106. For example, sensor 144 may include a pressure sensor that may be located in right ventricle 118. In these examples, sensor 144 may generate signals that indicate pressure sensed in right ventricle 118. Signals generated by sensor 144 may include higher frequency components that indicate pressure associated with contractions of heart 102 and lower frequency components that indicate pressure associated with breathing of patient 104. The lower frequency components of the signal may be generated by the variance in pressure within the chest accompanied by inhalation (e.g., an increase in pressure) and exhalation (e.g., a decrease in pressure). Processing module 132 may determine the breathing rate and/or breathing phase of patient 104 based on signals received from sensor 144. In some examples, processing module 132 may also monitor breathing parameters of patient 104 based on a thoracic impedance measured between electrodes 124, 126, as described herein.

Modules included in IMD 106 represent functionality that may be included in IMD 106 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

The techniques described in this disclosure, including those attributed to processing module 132, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in stimulators, programmers or other devices. The term "processor," "processing module" or "processing circuitry" may generally refer to any of the foregoing logic circuitry, alone or in combination with other logic circuitry, or any other equivalent circuitry.

Processing module 132 may communicate with memory 134. Memory 134 may include computer-readable instructions that, when executed by processing module 132, cause processing module 132 to perform the various functions attributed to processing module 132 herein. Memory 134 may include any volatile, non-volatile, magnetic, or electrical media, such as RAM, ROM, NVRAM, EEPROM, Flash memory, or any other digital media. Memory 134 may also include modified pacing parameters that define, for example, how processing module 132 may incrementally increase the pacing rate and incrementally decrease the pacing rate while the patient is in the resting state.

Processing module 132 may communicate with signal generator module 136 and electrical sensing module 138. Signal generator module 136 and electrical sensing module 138 are electrically coupled to electrodes 126 of leads 112, 114, 116 and housing electrode 124. Electrical sensing module 138 is configured to monitor signals from electrodes 124, 126 in order to monitor electrical activity of heart 102. Electrical sensing module 138 may selectively monitor cardiac signals via any bipolar or unipolar combination of electrodes 124, 126.

Signal generator module 136 may generate and deliver electrical stimulation therapy to heart 102 via electrodes 124, 126. Electrical stimulation therapy may include at least one of pacing pulses, ATP therapy, cardioversion therapy, and defibrillation therapy. Processing module 132 may control signal generator module 136 to deliver electrical stimulation therapy to heart 102 according to one or more therapy programs, which may be stored in memory 134. For example, processing module 132 may control signal generator module 136 to deliver pacing pulses to heart 102 based on one or more therapy programs and signals received from electrical sensing module 138. In other examples, processing module 132 may control signal generator module 136 to deliver at least one of ATP therapy, cardioversion therapy, and defibrillation therapy when processing module 132 detects a tachyarrhythmia.

Communication module 140 includes any suitable hardware, firmware, software or any combination thereof for communicating with another device, such as programmer 130 and/or a patient monitor. Under the control of processing module 132, communication module 140 may receive downlink telemetry from and send uplink telemetry to programmer 130 and/or a patient monitor with the aid of an antenna (not shown) in IMD 106.

Electrical sensing module 138 may include signal conditioning circuits, e.g., amplification and filtering circuits that amplify and filter cardiac electrical signals received from electrodes 124, 126. Processing module 132 may receive raw data (i.e., digitized cardiac electrical signals) from electrical sensing module 138 and detect cardiac events based on the raw data. For example, processing module 132 may analyze the raw data to determine the heart rate of patient 104 and to detect arrhythmias using any suitable arrhythmia detection algorithm.

In some examples, processing module 132 may control signal generator module 136 and electrical sensing module 138 to measure impedance between any combination of electrodes 124, 126. Processing module 132 may monitor breathing parameters of patient 104 based on the measured impedance. For example, processing module 132 may detect inhalation and exhalation based on the measured impedance. Additionally, processing module 132 may determine the breathing rate of patient 104 based on the measured impedance.

In examples where processing module 132 measures impedance between two of electrodes 124, 126, signal generator module 136 may be configured to generate a test current between the two electrodes and electrical sensing module 138 may be configured to measure a voltage generated across the electrodes in response to the generated current. Processing module 132 may control signal generator module 136 to generate the test current between the two electrodes, and processing module 132 may control electrical sensing module 138 to measure the voltage generated across the two electrodes. Processing module 132 may then determine the impedance between the two selected electrodes based on the amount of test current generated by signal generator module 136 and the voltage measured by electrical sensing module 138, e.g., using ohms law.

The measured impedance may change along with breathing of patient 104. For example, the measured impedance may increase along with inhalation and may decrease along with exhalation. Processing module 132 may determine the breathing phase (e.g., inhalation or exhalation) based on the measured impedance. For example, processing module 132 may determine that patient 104 is inhaling while the value of the measured impedance is increasing, and processing module 132 may determine that patient 104 is exhaling while the value of the measured impedance is decreasing. In some examples, processing module 132 may determine the patient's breathing rate based on the number of breathing cycles that occur within a period of time. In some examples, processing module 132 may determine a tidal volume based on the measured impedance.

Processing module 132 may select two electrodes that are spaced as far across the chest of patient 104 as possible in order to include more of the lung of patient 104 in the impedance field. For example, processing module 132 may select housing electrode 124 and an electrode in heart 102. In some examples, the impedance measurements may be calibrated on a patient-by-patient basis so that processing module 132 may determine the above breathing parameters based on a measured impedance that may be specific to patient 104.

Figure 4:
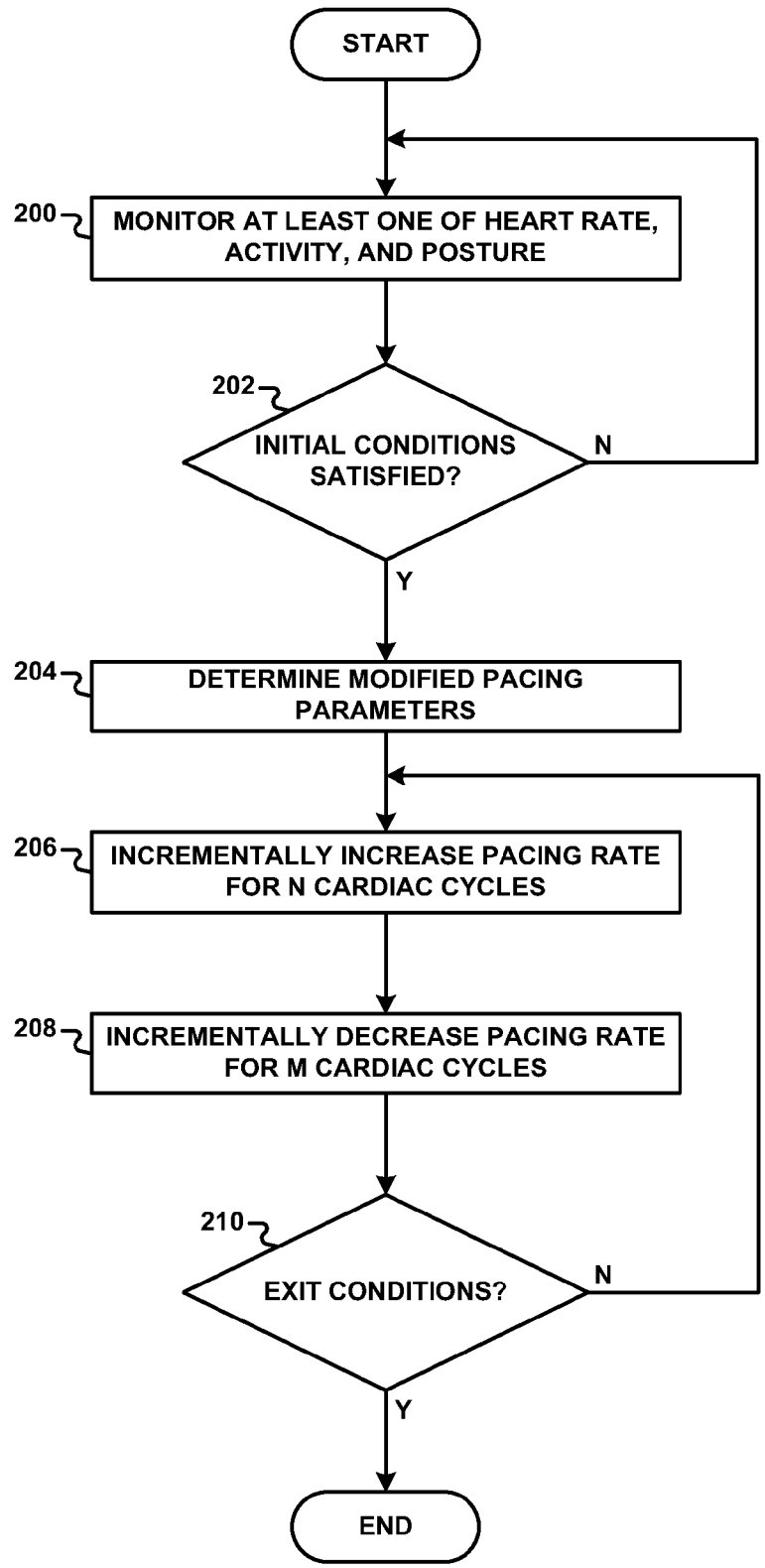
FIG. 4 is a flow diagram showing a method for controlling a breathing rate of the patient by modulating the cardiac pacing rate in an open-loop mode.

FIG. 4 shows a method for controlling a breathing rate of a patient by modulating the cardiac pacing rate in an open-loop mode. Processing module 132 may modify pacing in the open-loop mode according to the method of FIG. 4 without measuring breathing parameters using either impedance measurements or ventricular pressure measurements from sensor 144. Accordingly, the method of FIG. 4 may be implemented by IMD 106 even when components of IMD 106 (e.g., processing module 132, signal generator module 136, and electrical sensing module 138) do not include the requisite functionality for monitoring breathing parameters of patient 104. In some examples, since the method of FIG. 4 may be implemented by an IMD that does not monitor breathing parameters, IMDs that are currently implanted in patients which do not include this functionality may be reprogrammed to implement the method of FIG. 4 in order to control the breathing of a patient via cardiac pacing modulation.

Initially, during normal operation of IMD 106, processing module 132 may monitor at least one of heart rate, activity level, and posture of patient 104 to determine whether one or more initial conditions are satisfied (e.g., to determine whether patient 104 is resting and/or inactive) (200)-(202). Detection of one or more of the initial conditions may, in some examples, reliably indicate that patient 104 is at rest and/or inactive, while absence of the initial conditions may indicate that patient 104 is not likely at rest and/or is active. Initial conditions may include a heart-rate initial condition, an activity-level initial condition, and a posture-based initial condition. Processing module 132 may monitor at least one of heart rate, activity level of patient 104, and posture of patient 104, in order to determine whether the one or more initial conditions are satisfied.

In some examples, processing module 132 may determine that the heart-rate initial condition is satisfied when the monitored hear rate of patient 104 has been less than a threshold heart rate for a period of time referred to hereinafter as a "resting period." For example, a resting heart rate may include heart rates from 60-70 beats per minute for a typical person. The threshold heart rate may be set within this range of 60-70 beats per minute. The resting period may include a length of time that may reliably indicate that a person is at rest and may tend to stay at rest. For example, the resting period may be on the order of 5-15 minutes, although other periods of time are contemplated. In some examples, processing module 132 may modify the length of the resting period based on various factors. For example, processing module 132 may vary the length of the resting period based on the time of day. In one example, at night, processing module 132 may shorten the resting period since a person may tend to stay at rest for long periods of time at night. During the daytime, processing module 132 may lengthen the resting period since a person may be more active during the daytime, and may not rest for long periods. The threshold heart rate and the resting period may be programmed by a clinician on a patient-by-patient basis based on a patient's typical resting heart rate and typical activity level.

In some examples, processing module 132 may determine that the activity-level initial condition is satisfied when a monitored activity level of patient 104 is less than a threshold activity level. Processing module 132 may determine the activity level of patient 104 based on, for example, signals received from sensor 144 when sensor 144 includes a motion sensor such as an accelerometer and/or gyroscopic sensor. When sensor 144 includes an accelerometer and/or a gyroscopic sensor, the signals generated by sensor 144 may generally indicate an amount of movement (e.g., translation or rotation) of patient 104, and therefore may indicate how active patient 104 is at a current time. A minimal activity level, e.g., lack of motion, of patient 104 may indicate that patient 104 is at rest and/or inactive, while an activity level that deviates from the minimal activity level may indicate that patient 104 is initiating an activity. The threshold activity level may be selected such that the threshold activity level indicates that patient 104 may be too active to successfully implement control of the patient's respiration. Processing module 132 may determine that the activity-level initial condition is satisfied when the monitored activity level is less than the threshold activity level for a period of time. Processing module 132 may determine that the activity-level initial condition is not met when the monitored activity level has been greater than the threshold activity level within the period of time.

In some examples, processing module 132 may determine whether the posture-based initial condition is satisfied based on a monitored posture of patient 104. Processing module 132 may determine the posture of patient 104 based on signals received from sensor 144, e.g., when sensor 144 includes an accelerometer and/or gyroscopic sensor. Processing module 132 may determine that the posture-based initial condition is met when the monitored posture of patient 104 indicates that patient 104 may be in a resting and/or inactive posture, e.g., reclined or lying down, since a resting posture may indicate that patient 104 is at rest and may tend to stay at rest for a period of time. Processing module 132 may determine that the posture-based initial condition is not satisfied when the monitored posture of the patient indicates that patient 104 may be in an active position, e.g., when sensor 144 indicates that patient 104 is upright.

If processing module 132 determines that the initial conditions are not satisfied (e.g., that patient 104 is not at rest) in block (202), processing module 132 may continue monitoring at least one of heart rate, activity level, and posture in block (200). Processing module 132 may also continue to provide pacing therapy to heart 102, as normal, e.g., according to typical patient parameters for patient 104.

If processing module 132 determines that one or more initial conditions are satisfied (e.g., that patient 104 is at rest and/or inactive) in block (202), processing module 132 may determine modified pacing parameters (204). Modified pacing parameters may define the cardiac pacing rate delivered to heart 102 over a period of time while the one or more initial conditions are satisfied (e.g., while patient 104 is at rest and/or inactive). Modified pacing parameters may include parameters that control the amount (e.g., the incremental value) by which the pacing rate is incremented, the amount (e.g., the incremental value) by which the pacing rate is decremented, the number of cycles for which the pacing rate is incrementally increased, and the number of cycles for which the pacing rate is incrementally decreased. In some examples, modified pacing parameters may be predetermined values stored in memory 134, e.g., programmed into memory 134 by a clinician based on tests performed on patient 104 to determine the resting heart rate and breathing rate of patient 104. In other examples, modified pacing parameters may be determined based on other parameters sensed by IMD 106 when processing module 132 determines that the one or more initial conditions are satisfied (e.g., when processing module 132 determines that patient 104 is at rest and/or inactive). For example, modified pacing parameters may be based on at least one of a resting heart rate of patient 104 as determined by processing module 132 and a target breathing rate of patient 104.

Processing module 132 may control the pacing rate based on the modified pacing parameters in blocks (206) and (208). For example, processing module 132 may incrementally increase the pacing rate (i.e., decrement R-R pacing intervals) for N cardiac cycles (206), then incrementally decrease the pacing rate for M cardiac cycles (208). M and N may be integer values that are greater than 1, and in some examples, N may be equal to M. Processing module 132 may then determine whether exit conditions are present (210), as described hereinafter. If exit conditions are not present, processing module 132 may continue to incrementally increase the pacing rate for N cardiac cycles (206) and incrementally decrease the pacing rate for M cardiac cycles (208). However, if exit conditions are met, the method of FIG. 4 may end, and processing module 132 may return to pacing heart 102 normally, e.g., according to typical patient parameters for patient 104.

In general, processing module 132 may incrementally increase and incrementally decrease the pacing rate to approximate a pacing pattern that imitates RSA. This pacing pattern, generated by IMD 106 in blocks (206) and (208) may be referred to as an "RSA pacing pattern." As described above, during typical RSA, a patients heart rate may increase during inhalation and decrease during exhalation. The RSA pacing pattern generated by processing module 132 may be similar to this natural heart rate pattern that occurs during RSA.

The RSA pacing pattern generated by processing module 132 may be generated based on at least one of the resting heart rate of patient 104, a typical breathing rate for patient 104 while patient 104 is at rest, and the target breathing rate for patient 104. Patient 104 may have a typical resting heart rate (e.g., heartbeats per minute) and a typical resting breathing rate (e.g., breaths per minute). It follows then that patient 104 may have a typical number of heart beats per breathing cycle (e.g., heartbeats per minute divided by breaths per minute) when at rest and/or relatively inactive.

Processing module 132 may generate the RSA pacing pattern based on the typical number of heart beats per breathing cycle for patient 104. For example, processing module 132 may divide the total approximate number of heart beats per breathing cycle by two, then generate a first half of the RSA pacing pattern, in which the pacing rate is incrementally increased, using a first number of pacing pulses equal to the total number of heart beats per breathing cycle divided by two. Processing module 132 may generate a second half of an RSA pacing pattern, in which the pacing rate is incrementally decreased, using a second number of pacing pulses equal to the total number of heart beats per breathing cycle divided by two. Processing module 132 may spread the total number of pacing pulses delivered during the RSA pacing pattern over a time period that is equal to the target breathing period (e.g., 1/(target breathing rate)). The time period over which processing module 132 spreads the total number of pacing pulses delivered during the RSA pacing pattern may be referred to as an "RSA pacing period." For example, a single RSA pacing period may include pacing pulses delivered at an incrementally increased pacing rate and an incrementally decreased pacing rate according to blocks (206) and (208).

In a numerical example, a typical resting heart rate may be approximately 60 beats per minute and a typical breathing rate may be approximately 10 breaths per minute, yielding approximately 6 beats per breath. In this numerical example, processing module 132 may generate an RSA pacing pattern in which processing module 132 incrementally increases the pacing rate for the first 3 beats of the RSA pacing pattern and incrementally decreases the pacing rate for the subsequent 3 beats of the RSA pacing pattern, and then repeats this RSA pacing pattern until exit conditions are detected at block (210). Although processing module 132 may equally divide the number of pacing pulses applied to each half of the RSA pacing pattern in some examples, in other examples, the number of pacing pulses applied to each half of the RSA pacing pattern may not divide equally into two even parts because the approximate number of beats per breath may not always yield an integer value when divided by two. Accordingly, in some examples, processing module 132 may incrementally increase the pacing rate for a greater than half of the pulses applied during the RSA pacing pattern and incrementally decrease the pacing rate for less than half the pulses applied during the RSA pacing pattern. In other examples, processing module 132 may incrementally increase the pacing rate for less than half of the pulses applied during the RSA pacing pattern and incrementally decrease the pacing rate for greater than half the pulses applied during the RSA pacing pattern.

The amount by which processing module 132 incrementally increases and incrementally decreases the pacing rate may be based on the typical resting heart rate of patient 104. In some examples, processing module 132 may incrementally increase/decrease the pacing rate by a percentage of the resting heart rate during each successive pacing pulse (e.g., 10-20%). In other examples, processing module 132 may incrementally increase and incrementally decrease the pacing rate based on the current heart rate of patient 104. For example, processing module 132 may incrementally increase/decrease the pacing rate by a percentage of the currently detected heart rate during each successive pacing pulse.

The amount by which to increase/decrease the pacing rate may depend on a peak heart rate setting, determined, for example, based on the resting heart rate of patient 104. The amount may also be based on an inspiratory/expiratory ratio (e.g., 1:1 or 1:3, etc). In one example, the peak heart rate may be set to approximately 72 bpm, assuming a peak rate that is set at approximately 20% greater than a resting heart rate of 60 bpm. In this example, processing module 132 may increase/decrease the pacing rate towards the peak heart setting gradually over a plurality of cardiac cycles, eventually peaking out the pacing rate at the peak heart rate setting over approximately half of a predicted breathing cycle. For example, if the target breathing rate is at 10 breaths per min, the inspiratory/expiratory ratio is 1:1, and the current heart rate is 60 bpm, processing module 132 may calculate the time to reach the peak heart rate of 72 bpm as 3 seconds. Processing module 132 may then gradually increase the pacing rate during the 3 second period to the peak heart rate, then gradually decrease the pacing rate during the next 3 second period.

Figure 5:
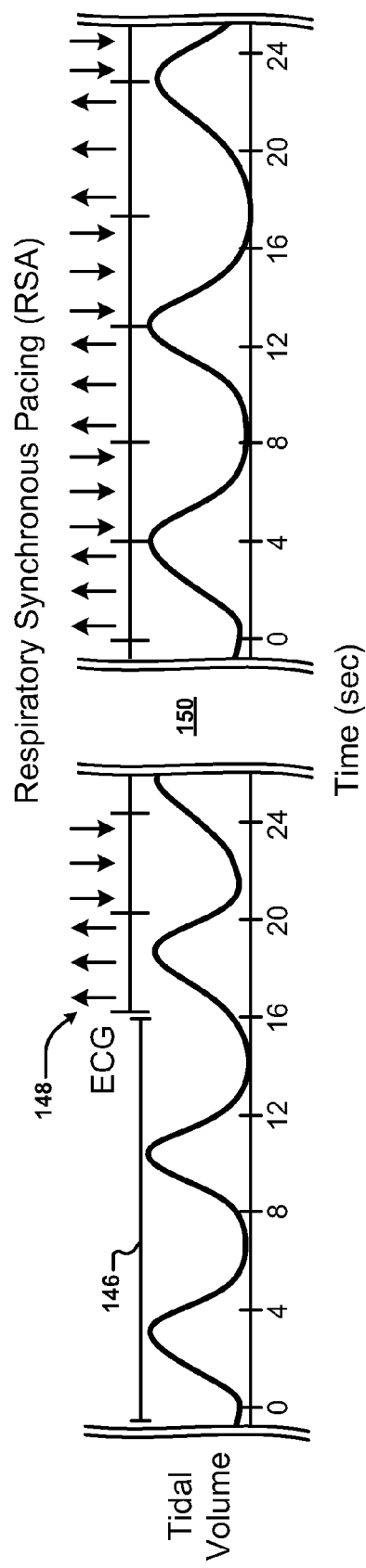
FIG. 5 is a graph showing a conceptual estimation of how a breathing pattern of the patient may be affected by implementation of the method of FIG. 4.

FIG. 5 shows a conceptual estimation of how a patient's (e.g., patient 104) breathing pattern may be affected by implementation of the method of FIG. 4. In particular, FIG. 5 shows a trace of a waveform for tidal volume. The tidal volume trace may represent the volume of air being displaced while patient 104 is breathing. A positive sloping region of the tidal volume trace from a valley of the tidal volume trace to a peak of the tidal volume trace may represent inhalation of patient 104. The negative sloping region of the tidal volume trace from a peak of the tidal volume trace to a valley of the tidal volume trace may represent exhalation of patient 104. Each breathing cycle of patient 104 may include a region of the tidal volume trace from a valley of the tidal volume trace to the next valley of the tidal volume trace.

The region 146 of FIG. 5 spanning from the left of the tidal volume trace to approximately 16 seconds may indicate a period of time during which processing module 132 controls pacing normally, e.g., not according to the modified pacing parameters. During region 146, processing module 132 may have detected that one or more of the initial conditions is satisfied (e.g., detected that patient 104 is at rest and/or inactive), e.g., based on a heart rate that is less than the threshold heart rate for the resting period.

Processing module 132 may determine the modified pacing parameters, e.g., according to block (204) of FIG. 4, upon detection that one or more of the initial conditions is satisfied. At 148, processing module 132 may begin controlling the pacing rate according to the modified pacing parameters. The up and down arrows "↑" and "↓", depending on direction, may indicate whether processing module 132 is incrementally increasing the pacing rate or incrementally decreasing the pacing rate. The regions including arrows pointing up ("↑") may indicate that processing module 132 is incrementally increasing the pacing rate. The regions including arrows pointing down ("↓") may indicate that processing module 132 is incrementally decreasing the pacing rate. Note that since processing module 132 may not measure breathing parameters in the example of FIG. 4, the incremental increasing/decreasing of the pacing rate may not start in phase with the breathing phase of patient such that an RSA pacing pattern is reproduced. In other words, upon initial control of pacing according to the modified pacing parameters, processing module 132 may not be incrementally increasing the pacing rate upon inhalation of patient 104 and incrementally decreasing the pacing rate upon exhalation of patient 104. Instead, the incremental increase/decrease in pacing rate may be out of phase as compared to typical RSA.

Over a period of time, conceptually illustrated by gap 150 between the left and right portions of FIG. 5, respiration of patient 104 may be synchronized, i.e., "sync," with the RSA pacing pattern produced by processing module 132. For example, after a period of time during which processing module 132 has implemented an RSA pacing pattern, patient 104 may tend to inhale while processing module 132 is increasing the rate of pacing, and patient 104 may tend to exhale while processing module 132 is decreasing the rate of pacing. In other words, the breathing phase of patient 104 may tend to align with the RSA pacing pattern such that the correlation between the RSA pacing pattern and the breathing pattern of patient 104 imitates naturally occurring RSA. The period of time illustrated by gap 150 may be variable.

The tendency of the breathing pattern of patient 104 to align with the RSA pacing pattern may be a phenomenon that occurs over a period of seconds to a period of minutes. Although the breathing pattern and RSA pacing pattern are illustrated as in phase with one another, such that naturally occurring RSA is imitated on the right half of FIG. 5, in some examples, the breathing pattern and RSA pacing pattern may not remain exactly in phase, but may experience some shifting. RSA is thought to be an intrinsic resting function of the cardiopulmonary system that may improve respiratory gas exchange efficiency through matching alveolar ventilation and capillary perfusion throughout the respiration cycle. Alignment of the breathing cycle to the pacing pattern may occur because the body may try to bring the cardiopulmonary system to its optimal resting condition (through efferent and afferent signaling), thus improving respiratory gas exchange efficiency.

Since the breathing pattern of patient 104 may tend to align with the RSA pacing pattern in order to maintain optimal ventilation perfusion ratio (VQ ratio), in some examples, processing module 132 may modify the RSA pacing pattern in order to achieve a consistent breathing rate or the target breathing rate. For example, processing module 132 may apply the RSA pacing pattern in a consistent manner, e.g., using the same increments/decrements to the pacing rate, in order to promote a consistent breathing pattern. Additionally, in some examples, processing module 132 may modify the increments/decrements to the pacing rate in order to extend the length of the RSA pacing period. For example, processing module 132 may increase the amount of time for which processing module 132 increments the pacing rate and decrements the pacing rate. In this manner, the breathing rate of patient 104 may decrease as the breathing pattern of patient 104 aligns with the RSA pacing pattern having an extended length.

Referring back to FIG. 4, as described above, processing module 132 may generate the RSA pacing pattern until exit conditions are detected in block (210). Exit conditions may include any detected conditions that may indicate that patient 104 is no longer at rest and/or that patient 104 has become active. When one or more exit conditions are detected, processing module 132 may discontinue pacing according to blocks (206) and (208) and return to pacing heart 102 normally. Processing module 132 may monitor at least one of heart rate, activity level, and posture of patient 104 in order to detect exit conditions.

In some examples, processing module 132 may determine that an exit condition exists when processing module 132 determines that the heart rate of patient 104 is greater than the threshold heart rate. In some examples, processing module 132 may determine that an exit condition exists when processing module 132 detects that the activity level of patient 104 is greater than the threshold activity level. In some examples, processing module 132 may determine that an exit condition exists when processing module 132 determines that the posture of patient 104 has transitioned from a resting posture to a more active posture, e.g., when the posture of patient 104 has transitioned from lying down to standing upright.

In other examples, processing module 132 may modify the pacing rate in blocks (206) and (208) for a predetermined period of time after processing module 132 determines that the one or more initial conditions are satisfied (e.g., that patient 104 is at rest and/or inactive) (e.g., approximately 15-60 minutes). In these examples, processing module 132 may determine that an exit condition exists when a predetermined period of time has passed since processing module 132 detected that the one or more initial conditions were satisfied in block (202). Therefore, processing module 132 may end the method of FIG. 4 when the predetermined period of time has passed since processing module 132 detected that the one or more initial conditions were satisfied (e.g., that patient 104 was at rest and/or inactive). In scenarios where patient 104 is treated for sleep apnea, the predetermined period of time may be on the order of hours.

In some examples, processing module 132 may modify the pacing rate in blocks (206) and (208) for a predetermined number of cardiac cycles after processing module 132 determines that one or more initial conditions are satisfied. In these examples, processing module 132 may determine that an exit condition exists when a predetermined number of cardiac cycles has passed since processing module 132 detected that the one or more initial conditions were satisfied in block (202). Therefore, processing module 132 may end the method of FIG. 4 when the predetermined number of cardiac cycles has passed since processing module 132 detected that the one or more initial conditions were satisfied (e.g., that patient 104 was at rest and/or inactive).

Although the method of FIG. 4 may be implemented by IMD 106 when IMD 106 does not include components that monitor breathing parameters, in some examples, when IMD 106 includes components that monitor breathing parameters, the method of FIG. 4 may be modified to include the measurement of breathing parameters, such as the breathing rate.

FIG. 6 shows a method for controlling the breathing rate of a patient via cardiac pacing modulation based on an initially determined breathing rate. Blocks (200) and (202) of FIG. 6 may include similar operations as blocks (200) and (202) described with respect to FIG. 4. If processing module 132 determines that one or more initial conditions are satisfied (e.g., determines that patient 104 is at rest and/or inactive) in block (202), processing module 132 may determine the breathing rate of patient 104 (300). For example, processing module 132 may determine the patient's breathing rate based on the number of breathing cycles that occur within a period of time.

Processing module 132 may determine modified pacing parameters in block (302). In some examples, block (302) may include similar operations as block (204). Additionally, or alternatively, processing module 132 may determine modified pacing parameters in block (302) based on the breathing rate determined in block (300).

In some examples, processing module 132 may determine a target breathing rate for patient 104 based on the current breathing rate and the current heart rate, then generate an RSA pacing pattern to achieve the target breathing rate. For example, processing module 132 may set the target breathing rate to a rate that is at the current breathing rate or that is slightly lower than the current breathing rate, e.g., to a lower rate of approximately 8-10 breaths per minute in some examples. In other examples, when the current breathing rate of patient 104 is higher (e.g., 15-20 breaths per minute), processing module 132 may set the target breathing rate to a fraction of the current breathing rate, e.g., 75-90% of the current breathing rate. After processing module 132 has generated the RSA pacing pattern for a period of time, the breathing rate of patient 104 may tend to align with the target breathing rate.

Processing module 132 may generate the RSA pacing pattern to achieve the target breathing rate by generating an RSA pacing pattern having a period that is approximately equal to the length of a breathing cycle at the target breathing rate. Processing module 132 may determine the number of pacing pulses to generate during the RSA pacing pattern based on the current heart rate of patient 104 and the target breathing rate. For example, processing module 132 may generate a similar number of pacing pulses during the RSA pacing pattern as the number of pacing pulses that would occur during one breathing cycle of patient 104 at the target breathing rate. Processing module 132 may then determine an amount by which to incrementally increase and incrementally decrease the pacing rate during the RSA pacing pattern. As described above, processing module 132 may incrementally increase the pacing rate and incrementally decrease the pacing rate during the RSA pacing pattern by a percentage of the resting heart rate during each successive beat.

After determining the modified pacing parameters (e.g., the RSA pacing pattern), processing module 132 may incrementally increase the pacing rate for the first portion of the RSA pacing pattern (304) and then incrementally decrease the pacing rate for the second portion of the RSA pacing pattern (306) according to the modified pacing parameters determined in block (302). Processing module 132 may then determine whether exit conditions are present (308). If exit conditions are not present, processing module 132 may continue to incrementally increase the pacing rate (304) and incrementally decrease the pacing rate (306). However, if exit conditions are satisfied, the method of FIG. 6 may end, and processing module 132 may return to pacing heart 102 normally. In some examples, block (308) may include similar operations as block (210). For example, processing module 132 may determine that an exit condition exists in block (308) when processing module 132 determines that at least one of the heart rate of patient 104 is greater than the threshold heart rate, that the activity level of patient 104 is greater than the threshold activity level, and that the posture of patient 104 has transitioned from a resting posture to a more active posture.

Generating the RSA pacing pattern based on a determined breathing rate in FIG. 6 may provide a more relevant RSA pacing pattern than the RSA pacing pattern generated in FIG. 4 that may not be based on a determined breathing rate. The RSA pattern generated in FIG. 6 based on a determined breathing rate may be better tailored to patient 104 at the time the one or more initial conditions are satisfied (e.g., at the time patient is at rest and/or inactive) because processing module 132 may generate an RSA pacing pattern that is based on current breathing conditions of patient, e.g., a current breathing rate, whereas processing module 132, according to the method of FIG. 4, estimated the current breathing parameters of patient 104 based on typical breathing parameters. In one example, if a current breathing rate is not determined prior to generating the RSA pacing pattern, there may be a greater likelihood that the target breathing rate may be further from the actual current breathing rate of patient 104. In this example, the breathing rate of patient 104 may not tend to align as quickly with the target breathing rate as would be the case if the RSA pacing pattern was generated to initially produce a similar breathing rate as the actual breathing rate of patient 104.

Referring now to FIG. 7, in some examples, processing module 132 may update the target breathing rate of the patient more frequently than in FIG. 4 and FIG. 6. In the example method of FIG. 7, after processing module 132 determines that one or more initial conditions are satisfied (e.g., determines that patient 104 is resting and/or inactive) at block (202), processing module 132 may enter into a control loop in which processing module 132 may determine the breathing rate of patient 104 as frequently as once per RSA pacing period. For example, processing module 132 may continuously monitor the breathing rate of patient 104 (300), determine modified pacing parameters (304), incrementally increase the pacing rate (304), and incrementally decrease the pacing rate (306), until processing module 132 detects exit conditions at (308).

In some examples according to the method of FIG. 7, processing module 132 may determine the breathing rate of patient 104 at block (300) during each loop back from block (308). In other words, processing module 132 may update the RSA pacing pattern after each iteration of the RSA pacing pattern based on a determined breathing rate at block (300). In some scenarios, when the RSA pacing pattern is in phase with the breathing pattern of patient 104 such that processing module 132 incrementally increases/decreases the pacing rate during inhalation/exhalation of patient 104, the RSA pacing pattern may be updated as often as once per breathing cycle of patient 104.

However, in some examples, determination of breathing rate at block (300) for each loop back from block (308) may not prove to be an effective method for modulating breathing rate since the tendency for the breathing rate to align with the RSA pacing pattern may not manifest itself immediately during the next breathing cycle, but may manifest itself after a plurality of breathing cycles. Accordingly, in some examples, processing module 132 may not determine a new breathing rate in block (300) and update the modified pacing parameters in block (302) during each loop back to block (300), but may instead, determine the breathing rate at block (300) and update the modified pacing parameters at block (302) after a predetermined number of breathing cycles, a predetermined number of cardiac cycles, or a predetermined period of time (e.g., approximately 5-10 minutes).

Generating the RSA pacing pattern based on a determined breathing rate more frequently, as in FIG. 7, may provide a more relevant RSA pacing pattern than even the RSA pacing pattern generated in FIG. 6 since the RSA pattern generated in FIG. 7 may be more tailored to patient 104 at the time the RSA pacing pattern is generated. Processing module 132 may return to normal pacing upon detection of exit conditions in block (308).

In examples where IMD 106 is configured to measure breathing parameters, e.g., according to FIGS. 6-7, processing module 132 may determine the phase of the breathing cycle of patient 104 and control the pacing rate based on the current phase of the breathing cycle. For example, IMD 106 may determine when patient 104 is inhaling and when patient 104 is exhaling based on a measured impedance, as described above. In examples where IMD 106 is configured to measure breathing parameters of patient 104, processing module 132 may control the pacing rate based on current breathing parameters, e.g., a current phase of the breathing cycle.

Processing module 132 may detect the phase of the breathing cycle of patient 104 and initiate the RSA pacing pattern based on the detected phase (e.g., based on detection of inhalation or exhalation). In some examples, when processing module 132 is configured to determine a current breathing cycle phase, processing module 132 may selectively initiate the RSA pacing pattern (e.g., blocks (304)-(306) of FIGS. 6-7) upon detection of inhalation by patient 104. In these examples, processing module 132 may begin incrementally increasing the pacing rate for N cardiac cycles at block 304 upon detection that patient 104 is inhaling. Subsequent to detecting that patient 104 is inhaling, processing module 132 may continue performing the operations of either FIG. 6 or FIG. 7 until exit conditions are detected in block (308), as described above. In other words, processing module 132 may initially start the RSA pacing pattern of blocks 304-306 upon detection of inhalation after the initial conditions are satisfied in block (202), then, during subsequent loops (e.g., from blocks (304)-(308) in FIG. 6 or from blocks (300)-(308) in FIG. 7), processing module 132 may provide the RSA pacing pattern without detecting the phase of the breathing cycle of patient 104.

Generating the RSA pacing pattern initially based on a determined breathing cycle phase, e.g., in either of FIGS. 6-7, may initially provide a more appropriate RSA pacing pattern to patient 104 since processing module 132 may start the RSA pacing pattern in phase with the breathing pattern of patient 104. In other words, initially incrementally increasing the pacing rate for N cardiac cycles in block (304) upon detection of inhalation of patient 104 may be more appropriate than in other examples where processing module 132 does not determine the breathing phase of patient 104, and, therefore, may begin incrementally increasing the pacing rate during a time other than upon inhalation of patient 104 (e.g., during exhalation). Beginning the RSA pacing pattern based on the breathing phase of patient 104 (e.g., in response to detection of inhalation) may result in a faster alignment and tracking of the breathing pattern of patient 104 with the RSA pacing pattern.

FIGS. 8A-8B show modulation of pacing rate based on detected breathing parameters. FIG. 8A shows modulation of pacing parameters to imitate RSA based on a detected phase of the breathing cycle. In order to imitate RSA, processing module 132 may modulate the cardiac pacing rate based on a current detected phase of the breathing cycle. For example, processing module 132 may incrementally increase the pacing rate upon the detection of inhalation by patient 104, and incrementally decrease the pacing rate upon the detection of exhalation by patient 104. Processing module 132 may imitate RSA in this manner while one or more initial conditions are satisfied (e.g., while patient 104 is resting and/or inactive), or at other times.

Although controlling pacing in order to imitate RSA as illustrated in FIG. 8A shows that the incremental increases and incremental decreases of the pacing rate occur during exhalation and inhalation, respectively, in some examples, the changes in pacing rate may be slightly out of phase with the breathing cycle. In one example, since each breathing cycle may include a limited number of paced cardiac cycles (e.g., 6 cardiac cycles), processing module 132 may not control the pacing pulses with such resolution that the pacing pulses that are applied while incrementally increasing the pacing rate fall within the inhalation phase of patient 104. In a similar manner, processing module 132 may not control the pacing pulses with such resolution that the pacing pulses that are applied while incrementally decreasing the pacing rate fall within the exhalation phase of patient 104. Instead, in some examples, some of the pacing pulses targeted for the inhalation phase of patient 104 may be delivered at the beginning of the exhalation phase of patient 104. In a similar manner, some of the pacing pulses targeted for the exhalation phase of patient 104 may be delivered at the beginning of the inhalation phase of patient 104. In summary, the pacing pulses delivered by processing module 132 based on the current phase of the breathing cycle of patient 104 may either be in phase, or slightly out of phase, with the breathing cycle of patient 104 when processing module 132 attempts to imitate RSA.

In another example, the changes in pacing rate may be slightly out of phase with the breathing cycle due to detection issues with breathing parameters. For example, processing module 132 may not detect the exact moment at which inhalation of patient 104 transitions to exhalation. In other words, processing module 132 may not always detect the peaks in the tidal volume curve, and therefore, processing module 132 may not always incrementally increase and incrementally decrease the pacing rate at exactly the time the patient transitions from inhalation to exhalation. Accordingly, detection issues with determining the phase of the breathing cycle may cause the pacing rate to be slightly out of phase when processing module 132 attempts to imitate RSA.

FIG. 8B shows modulation of the pacing rate in a manner that may be referred to herein as "inverse RSA pacing." Processing module 132 may provide inverse RSA pacing by incrementally decreasing the pacing rate upon the detection of inhalation by patient 104, and by incrementally increasing the pacing rate upon detection of exhalation by patient 104. Inverse RSA pacing differs from RSA pacing that is slightly out of phase (as described above) in that during inverse RSA pacing, processing module 132 may continually control changes in the pacing rate so that the pacing rate is incrementally increased/decreased during exhalation/inhalation over a plurality of cardiac cycles, e.g., for approximately 5-10 minutes, or until a desired effect is detected. The amount of time for which inverse RSA pacing may be applied may vary by application. For example, the amount of time may be on the order of 10 seconds to 1 minute for treatment of a single pause in breathing (e.g., sleep apnea) or may be applied continuously overnight.

Inverse RSA pacing may cause the chemical makeup of the blood to change, which may in turn promote an increase in the breathing rate of patient 104. For example, inverse RSA pacing may cause an increase in carbon dioxide in the blood (e.g., an increased $PaCO_2$), which may in turn promote an increased breathing rate and/or tidal volume. Thus, in examples where IMD 106 is configured to measure breathing parameters, processing module 132 may generate inverse RSA pacing based on a detected phase of the breathing cycle in order to increase the breathing rate of patient 104 towards a target breathing rate.

Figure 9:
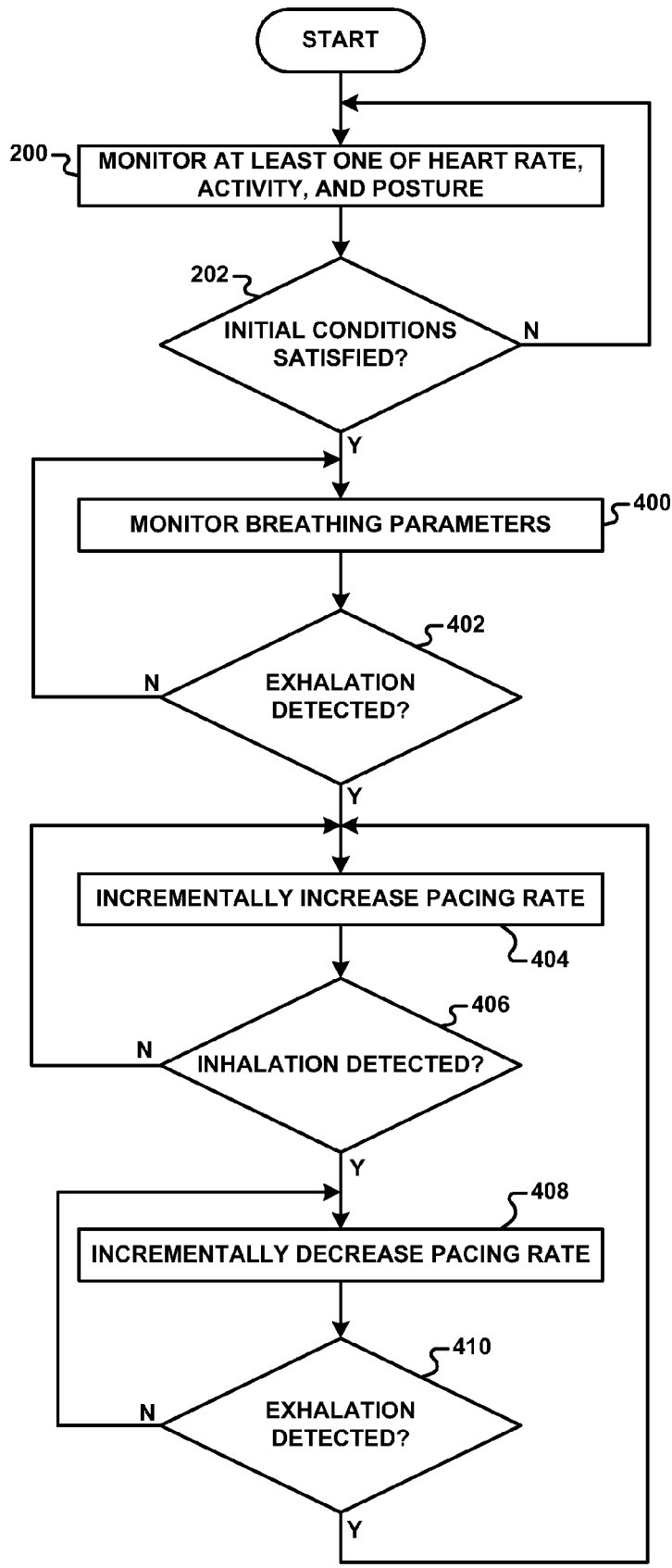
FIG. 9 is a flow diagram showing an example method for generating inverse RSA pacing based on a detected phase of the breathing cycle of the patient.

FIG. 9 shows an example method for generating inverse RSA pacing based on a detected phase of the breathing cycle of a patient. IMD 106 may provide inverse RSA pacing while one or more initial conditions are satisfied (e.g., while patient 104 is at rest and/or inactive). Blocks (200) and (202) of FIG. 9 may include similar operations as blocks (200) and (202) described with respect to FIG. 4. If processing module 132 determines that one or more initial conditions are satisfied (e.g., determines that patient 104 is at rest and/or inactive) in block (202), processing module 132 may monitor breathing parameters of patient 104 (400). For example, processing module 132 may determine the phase of the breathing cycle of patient 104.

Processing module 132 may detect whether patient 104 is exhaling (402). If processing module 132 detects that patient 104 is inhaling, processing module 132 may continue monitoring breathing parameters at block (400). If processing module 132 detects that patient 104 is exhaling, processing module 132 may begin incrementally increasing the pacing rate (404). Processing module 132 may incrementally increase the pacing rate based on the current heart rate of patient 104. In one example, processing module 132 may incrementally increase the pacing rate by a predetermined percentage of the resting heart rate.

While incrementally increasing the pacing rate, processing module 132 may monitor breathing parameters in order to detect inhalation of patient 104 (406). If inhalation is not detected at block (406), processing module 132 may continue increasing the pacing rate in block (404). Upon detection of inhalation at block (406), processing module 132 may begin incrementally decreasing the pacing rate (408). In one example, processing module 132 may incrementally decrease the pacing rate by a predetermined percentage of the resting heart rate.

Processing module 132 may continue to monitor the phase of the breathing cycle of patient 104 while incrementally decreasing the pacing rate in block (408). If processing module 132 does not detect exhalation (410), processing module 132 may continue incrementally decreasing the pacing rate in block (408). If processing module 132 detects exhalation, processing module 132 may begin incrementally increasing the pacing rate in block (404). In some examples, processing module 132 may discontinue pacing according to the method of FIG. 9 when processing module 132 determines that the breathing rate of patient 104 has increased to a rate that is greater than a threshold breathing rate.

Figure 10:
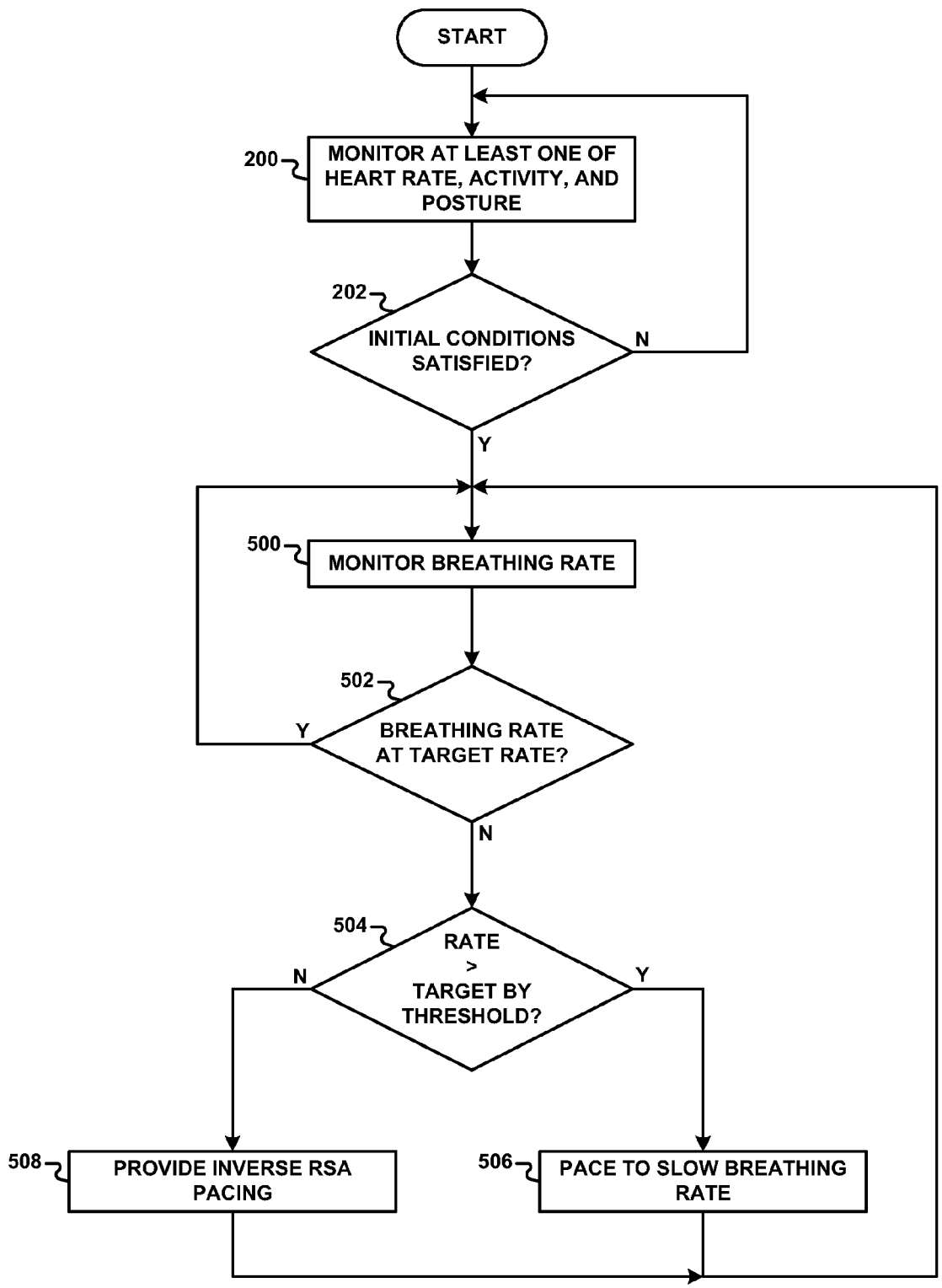
FIG. 10 is a flow diagram showing a method for controlling the breathing rate of the patient to match a target breathing rate.

FIG. 10 shows a method for controlling the breathing rate of a patient to match a target breathing rate. In some examples, the target breathing rate of FIG. 10 may be set by a clinician. Blocks (200) and (202) of FIG. 10 may include similar operations as blocks (200) and (202) described with respect to FIG. 4. If processing module 132 determines that one or more initial conditions are satisfied (e.g., that patient 104 is at rest and/or inactive) in block (202), processing module 132 may monitor a breathing rate of patient 104 (500).

Processing module 132 may then determine whether the breathing rate of patient 104 is approximately equal to the target breathing rate (502). If the breathing rate of patient 104 is approximately equal to the target breathing rate, processing module 132 may continue normal pacing and may continue monitoring the breathing rate of patient (500). For example, processing module 132 may determine that the breathing rate is approximately equal to the target breathing rate if the breathing rate is different than the target breathing rate by less than a threshold amount. If the breathing rate of patient 104 is not approximately equal to the target breathing rate, processing module 132 may determine whether the breathing rate is greater than the target breathing rate by the threshold amount (504).

If processing module 132 determines that the breathing rate is greater than the target breathing rate by the threshold amount, processing module 132 may implement an RSA pacing pattern according to the method of any of FIG. 4, FIG. 6, and FIG. 7 in order to slow the breathing rate of patient 104 (506). Implementation of the RSA pacing pattern according to any of these methods may decrease the breathing rate of patient 104 towards the target breathing rate, as described above. In other examples, instead of using a method according to any of FIG. 4, FIG. 6, and FIG. 7, processing module 132 may implement RSA pacing based on the detected phase of the breathing cycle of patient 104 as described with respect to FIG. 8A. After implementing the RSA pacing pattern in block (506), processing module 132 may monitor the breathing rate of patient 104 in block (500) and determine whether the breathing rate is approximately equal to the target breathing rate (502).

If processing module 132 determines that the breathing rate of patient 104 is not greater than the target breathing rate by the threshold amount in block (504), then, based on blocks (502) and (504), processing module 132 may determine that the breathing rate of patient 104 is less than the target breathing rate by greater than the threshold amount in block (504). Processing module 132 may then provide inverse RSA pacing based on a detected phase of the breathing cycle of patient 104 (508) in order to increase the breathing rate of patient 104. Processing module 132 may provide inverse RSA pacing according to the method of FIG. 9, for example, in order to increase the breathing rate of patient towards the target breathing rate. After providing inverse RSA pacing for a period of time, processing module 132 may monitor the breathing rate of patient 104 (500) and determine whether the breathing rate of patient 104 has increased to a rate that is approximately equal to the target breathing rate (502). IMD 106 may implement the method of FIG. 10 for a predetermined period of time. For example, in the case of sleep apnea, e.g., central sleep apnea, IMD 106 may implement the method of FIG. 10 for a period of hours during the night while patient 104 is sleeping.

The techniques described in this disclosure, including those attributed to processing module 132, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in stimulators, programmers or other devices. The term "processor," "processing module" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), static RAM (SRAM), electrically erasable programmable read-only memory (EEPROM), Flash memory, magnetic data storage media, optical data storage media, or the like. The instructions may be executed to support one or more aspects of the functionality described in this disclosure.

Various examples have been described. These and other examples are within the scope of the following claims.

The invention claimed is:
1. A method comprising:
controlling a cardiac pacing rate of an implantable medical device (IMD) to control a heart rate of a patient;
determining that the patient is in a resting state; and
modifying the pacing rate of the IMD for N cardiac cycles in response to determining that the patient is in the resting state, wherein N is an integer greater than 1, and wherein modifying the pacing rate comprises:
incrementally increasing the pacing rate for a first portion of the N cardiac cycles; and
incrementally decreasing the pacing rate for a second portion of the N cardiac cycles; and
discontinuing modification of the pacing rate when at least one of a predetermined amount of time has passed since determining that the patient is in the resting state and a predetermined number of cardiac cycles have passed since determining that the patient is in the resting state.

2. The method of claim 1, further comprising, before modifying the pacing rate of the IMD for N cardiac cycles, determining amounts by which to incrementally increase and incrementally decrease the pacing rate based on at least one of a current heart rate of the patient and a breathing rate of the patient.

3. A method comprising:
controlling a cardiac pacing rate of an implantable medical device (IMD) to control a heart rate of a patient;
determining that the patient is in a resting state; and
modifying the pacing rate of the IMD for N cardiac cycles in response to determining that the patient is in the resting state, wherein N is an integer greater than 1, and wherein modifying the pacing rate comprises:
incrementally increasing the pacing rate for a first portion of the N cardiac cycles;
incrementally decreasing the pacing rate for a second portion of the N cardiac cycles; and
determining, based on a target breathing rate of the patient, at least one of an amount by which to incrementally increase the pacing rate for each cardiac cycle of the first portion, an amount by which to incrementally decrease the pacing rate for each cardiac cycle of the second portion, and the number of cardiac cycles, N.

4. The method of claim 3, further comprising determining that the patient is in the resting state based on at least one of a sensed activity level of the patient and a posture of the patient.

5. The method of claim 3, wherein the first and second portions comprise all of the N cardiac cycles, and wherein the second portion occurs after the first portion.

6. The method of claim 3, wherein N is an integer that is less than or equal to 12.

7. A method comprising:
controlling a cardiac pacing rate of an implantable medical device (IMD) to control a heart rate of a patient;
determining that the patient is in a resting state; and
modifying the pacing rate of the IMD for N cardiac cycles in response to determining that the patient is in the resting state, wherein N is an integer greater than 1, and wherein modifying the pacing rate comprises:
incrementally increasing the pacing rate for a first portion of the N cardiac cycles;
incrementally decreasing the pacing rate for a second portion of the N cardiac cycles; and
determining a breathing rate of the patient; and
determining the number of cardiac cycles, N, for which to modify the pacing rate based on the determined breathing rate.

8. The method of claim 7, further comprising determining that the patient is in the resting state based on at least one of a sensed activity level of the patient and a posture of the patient.

9. The method of claim 7, wherein the first and second portions comprise all of the N cardiac cycles, and wherein the second portion occurs after the first portion.

10. The method of claim 7, wherein N is an integer that is less than or equal to 12.

11. A device comprising:
one or more electrodes configured for implantation in a patient;
a stimulation module configured to generate stimulation for delivery to the one or more electrodes; and
a processing module configured to:
control a cardiac pacing rate of the stimulation delivered to the one or more electrodes to control a heart rate of the patient;
determine that the patient is in a resting state; and
modify the pacing rate for N cardiac cycles in response to determining that the patient is in the resting state, wherein N is an integer greater than 1, and wherein modifying the pacing rate comprises:
incrementally increasing the pacing rate for a first portion of the N cardiac cycles; and
incrementally decreasing the pacing rate for a second portion of the N cardiac cycles; and
wherein the processing module discontinues modification of the pacing rate when at least one of a predetermined amount of time has passed since determining that the patient is in the resting state and a predetermined number of cardiac cycles have passed since determining that the patient is in the resting state.

12. The device of claim 11, wherein the processing module incrementally decreases the pacing rate to a value that is less than approximately 75% of the threshold heart rate.

13. The device of claim 11, wherein the processing module, before modifying the pacing rate of the IMD for N cardiac cycles, determines amounts by which to incrementally increase and incrementally decrease the pacing rate based on at least one of a current heart rate of the patient and a breathing rate of the patient.

14. The device of claim 11, wherein the processing module determines a breathing rate of the patient and determines the number of cardiac cycles, N, for which to modify the pacing rate based on the determined breathing rate.

15. A device comprising:
one or more electrodes configured for implantation in a patient;
a stimulation module configured to generate stimulation for delivery to the one or more electrodes; and
a processing module configured to:
control a cardiac pacing rate of the stimulation delivered to the one or more electrodes to control a heart rate of the patient;
determine that the patient is in a resting state; and
modify the pacing rate for N cardiac cycles in response to determining that the patient is in the resting state, wherein N is an integer greater than 1, and wherein modifying the pacing rate comprises:
incrementally increasing the pacing rate for a first portion of the N cardiac cycles; and
incrementally decreasing the pacing rate for a second portion of the N cardiac cycles; and
wherein the processing module determines, based on a target breathing rate of the patient, at least one of an amount by which to incrementally increase the pacing rate for each cardiac cycle of the first portion, an amount by which to incrementally decrease the pacing rate for each cardiac cycle of the second portion, and the number of cardiac cycles, N.

16. The device of claim 15, wherein the processing module determines that the patient is in the resting state based on at least one of a sensed activity level of the patient and a posture of the patient.

17. The device of claim 15, wherein the first and second portions comprise all of the N cardiac cycles, and wherein the second portion occurs after the first portion.

18. The device of claim 15, wherein N is an integer that is less than or equal to 12.

19. A device comprising:
one or more electrodes configured for implantation in a patient;
a stimulation module configured to generate stimulation for delivery to the one or more electrodes; and a processing module configured to:
- control a cardiac pacing rate of the stimulation delivered to the one or more electrodes to control a heart rate of the patient;
- determine a breathing rate of the patient; and
- determine the number of cardiac cycles, N, for which to modify the pacing rate based on the determined breathing rate
- determine that the patient is in a resting state; and
- modify the pacing rate for N cardiac cycles in response to determining that the patient is in the resting state, wherein N is an integer greater than 1, and wherein modifying the pacing rate comprises:
- incrementally increasing the pacing rate for a first portion of the N cardiac cycles; and
- incrementally decreasing the pacing rate for a second portion of the N cardiac cycles.

20. The device of claim 19, wherein the processing module determines that the patient is in the resting state based on at least one of a sensed activity level of the patient and a posture of the patient.

21. The device of claim 19, wherein the first and second portions comprise all of the N cardiac cycles, and wherein the second portion occurs after the first portion.

22. The device of claim 19, wherein N is an integer that is less than or equal to 12.

* * * * *